(12) United States Patent
Meinke et al.

(10) Patent No.: US 8,338,458 B2
(45) Date of Patent: Dec. 25, 2012

(54) METHOD OF TREATMENT USING FUSED AROMATIC COMPOUNDS HAVING ANTI-DIABETIC ACTIVITY

(75) Inventors: Peter T. Meinke, Scotch Plains, NJ (US); Andrew Denker, Boston, MA (US); Gary E. Meininger, Livingston, NJ (US); Naoto Uemura, Westfield, NJ (US); John A. Wagner, Westfield, NJ (US); Steven Charnick, Wayne, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 372 days.

(21) Appl. No.: 12/597,530

(22) PCT Filed: May 2, 2008

(86) PCT No.: PCT/US2008/005726
§ 371 (c)(1),
(2), (4) Date: Oct. 26, 2009

(87) PCT Pub. No.: WO2008/137105
PCT Pub. Date: Nov. 13, 2008

(65) Prior Publication Data
US 2010/0130521 A1 May 27, 2010

Related U.S. Application Data

(60) Provisional application No. 60/927,949, filed on May 7, 2007.

(51) Int. Cl.
*A61K 31/44* (2006.01)
(52) U.S. Cl. ........................................ 514/338; 514/866
(58) Field of Classification Search ................... 514/338, 514/866
See application file for complete search history.

(56) References Cited

U.S. PATENT DOCUMENTS 7,834,036 B2 * 11/2010 Wood et al. .................... 514/338
2006/0178514 A1 8/2006 Baruah et al.

FOREIGN PATENT DOCUMENTS

| WO | WO 01/30343 | 5/2001 |
|---|---|---|
| WO | WO 01/60807 | 8/2001 |
| WO | WO 02/08188 A1 | 1/2002 |
| WO | WO 02/10137 A2 | 2/2002 |
| WO | WO 02/10137 A3 | 2/2002 |
| WO | WO 02/064094 A2 | 8/2002 |
| WO | WO 02//064094 A3 | 8/2002 |
| WO | 03/055485 | 7/2003 |
| WO | WO 2004/014860 A2 | 2/2004 |
| WO | WO 2004/014860 A3 | 2/2004 |
| WO | WO 2004/019869 A2 | 3/2004 |
| WO | WO 2004/019869 A3 | 3/2004 |
| WO | WO 2004/020408 A1 | 3/2004 |
| WO | WO 2004/020409 A1 | 3/2004 |
| WO | WO 2006/033891 A2 | 3/2006 |
| WO | WO 2006/033891 A3 | 3/2006 |
| WO | 2006/083645 | 8/2006 |
| WO | WO 2006/096564 A1 | 9/2006 |
| WO | WO 2006/099077 A1 | 9/2006 |
| WO | WO 01/79197 | 1/2010 |

OTHER PUBLICATIONS

Supplemental European Search Report in EP 08767538, dated Sep. 19, 2011.
Adams, A. D. et al., "Amphipathic 3-Phenyl-7-propylbenzisoxazoles; Human PPaR γ, δ and α Agonists" Bioorganic & Medicinal Chemistry Letters, 2003, pp. 931-935, vol. 13.
Shutske, G.M. et al., "[(3-Aryl-1,2-benzisoxazol-6-yl)oxy]acetic Acids. A New Diuretic Series", J. Med. Chem, 1982, pp. 36-44, vol. 25.
Simionatto, E. L. et al., "The Effect of Boric Acid on the Dehydration Step in the Formation of Oxime from Salicylaldehyde", J. Chem. Soc. Perkin Trans, 1993, pp. 1291-1294, vol. 2.

* cited by examiner

*Primary Examiner* — Kevin E Weddington
(74) *Attorney, Agent, or Firm* — Anna L. Cocuzzo; Janet E. Fair; John C. Todaro

(57) ABSTRACT

Fused aromatic compounds of Formula I are PPAR gamma agonists or partial agonists and are useful for weekly dosing in the treatment or control of type II diabetes, including hyperglycemia, dyslipidemia, hyperlipidemia, hypercholesterolemia, hypertriglyceridemia, and obesity that are often associated with type 2 diabetes.

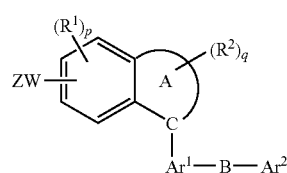

I

14 Claims, No Drawings

METHOD OF TREATMENT USING FUSED AROMATIC COMPOUNDS HAVING ANTI-DIABETIC ACTIVITY

CROSS-REFERENCE TO RELATED APPLICATIONS

This application is a U.S. National Phase application under 35 U.S.C. §371 of PCT Application No. PCT/US2008/005726, filed May 2, 2008, which published as WO 2008/137105 A1 on Nov. 13, 2008, and claims priority under 35 U.S.C. §119 from U.S. Provisional Application No. 60/927,949, filed May 7, 2007.

FIELD OF THE INVENTION

The instant invention is concerned with a method of treatment using fused aromatics in the treatment of Type 2 diabetes mellitus, and of conditions that are often associated with this disease, including obesity and lipid disorders.

BACKGROUND OF THE INVENTION

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced in the body. Patients having type 2 diabetes often have hyperinsulinemia (elevated plasma insulin levels); however, these patients are insulin resistant, which means that they have a resistance to the effect of insulin in stimulating glucose and lipid metabolism in the main insulin-sensitive tissues, which are muscle, liver and adipose tissues. Patients who are insulin resistant but not diabetic compensate for the insulin resistance by secreting more insulin, so that serum glucose levels are not elevated enough to meet the criteria of Type 2 diabetes. In patients with Type 2 diabetes, even elevated plasma insulin levels are insufficient to overcome the pronounced insulin resistance.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Many patients who have insulin resistance or Type 2 diabetes often have several symptoms that together are referred to as syndrome X, or the metabolic syndrome. A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

There are several available treatments for type 2 diabetes, each of which has its own limitations and potential risks. Included among these are physical exercise, a reduction in caloric intake, the administration of various antidiabetic agents, such as sulfonylureas (e.g. tolbutamide or glipizide), meglitinide (e.g. repaglinide or nateglinide), which are insulin secretagogues, biguanides, the two best known of which are phenformin and metformin, glitazones (i.e. 5-benzylthiazolidine-2,4-diones), such as rosiglitazone and pioglitazone, newer PPAR agonists, such as agonists of PPAR alpha, gamma and/or delta, PPAR alpha/gamma dual agonists, such as muraglitazar and tesaglitazar, and insulin.

There have been reports of compounds that are PPAR gamma antagonists or partial agonists. WO01/30343 describes a specific compound that is a PPAR partial agonist/antagonist that is useful for the treatment of obesity and Type 2 diabetes. WO02/08188, WO2004/020408, WO2004/020409, and WO2004/019869 disclose classes of PPAR agonists and partial agonists that are indole derivatives and that are useful in the treatment of Type 2 diabetes, with reduced side effects relating to body and heart weight gain. The compounds used in the present invention have been disclosed in WO2006/096564A1 published on Sep. 14, 2006. Surprisingly, none of the compounds or publications described relates to the use of the compounds addressed herein used in a once weekly dosing regimen. Moreover, none of the compounds described above demonstrates the benefits described herein when used pursuant to a weekly dosing regimen. Consequently, one aspect of the invention that is of importance relates to the weekly dosing regimen for the compounds described herein without significant weight gain. These and other benefits will be apparent from the teachings contained herein.

SUMMARY OF THE INVENTION

The present invention is directed to the treatment of type 2 diabetes in a mammalian patient in need of such treatment, comprising administering to the patient on a once weekly basis, a compound of formula I:

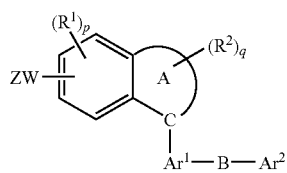

or a pharmaceutically acceptable salt or solvate thereof wherein:

Ring A is a 5- or 6-membered aromatic or heteroaromatic ring having 1-2 heteroatoms independently selected from O, S, and N, where Ring A together with the phenyl ring to which ring A is fused forms a naphthalene or benzoheteroaromatic ring;

Ar$^1$ and Ar$^2$ are each carbocyclic or heterocyclic aromatic groups which are independently selected from the group consisting of phenyl, naphthyl, pyridinyl, pyrazinyl, and pyrimidinyl, said aromatic groups being optionally substituted with 1-4 substituent groups independently selected from halogen, —C$_1$-C$_6$ alkyl, —C$_2$-C$_6$ alkenyl, —C$_2$-C$_6$ alkynyl, —OC$_1$-C$_6$ alkyl, —OC$_2$-C$_6$ alkenyl, —C(=O)C$_1$-C$_6$ alkyl, —S(O)$_n$C$_1$-C$_6$ alkyl, C$_3$-C$_7$ cycloalkyl, —OC$_3$-C$_7$ cycloalkyl, —NO$_2$, and —CN, wherein —C$_1$-C$_6$ alkyl, —C$_2$-C$_6$ alkenyl, —C$_2$-C$_6$ alkynyl, —OC$_1$-C$_6$ alkyl, —OC$_2$-C$_6$ alkenyl, —C(=O) C$_1$-C$_6$ alkyl, —S(O)$_n$C$_1$-C$_6$ alkyl, C$_3$-C$_7$ cycloalkyl, and —OC$_3$-C$_7$ cycloalkyl are each optionally substituted with 1-5 halogens;

B is selected from the group consisting of —O—, —S(O)$_n$—, —N(R$^3$)—, —C(=O)—, —C(R$^4$)$_2$—, and —C$_{3-6}$ cycloalkylidene-;

—WZ is selected from the group consisting of —O—C (R$^5$)(R$^6$)-Z, —S(O)$_n$—C(R$^5$)(R$^6$)-Z, and —CH$_2$—C(R$^5$)(R$^6$)-Z;

Z is selected from the group consisting of —CO$_2$R$^7$ and tetrazole;

R$^1$ and R$^2$ are each independently selected from the group consisting of halogen, —CN, —NO$_2$, —OH, —C$_1$-C$_5$ alkyl, —OC$_1$-C$_5$ alkyl, —C(=O)C$_1$-C$_5$ alkyl, —S(O)$_n$C$_1$-C$_5$alkyl, and C$_3$-C$_6$ cycloalkyl, wherein C$_1$-C$_5$ alkyl, —OC$_1$-C$_5$ alkyl, —C(=O)C$_1$-C$_5$ alkyl, —S(O)$_n$C$_1$-C$_5$alkyl, and C$_{3-6}$ cycloalkyl are optionally substituted with 1-5 halogens;

R$^3$ is selected from the group consisting of H and C$_1$-C$_5$ alkyl;

each R$^4$ is independently selected from the group consisting of H, halogen, and —C$_1$-C$_5$ alkyl, wherein —C$_1$-C$_5$ alkyl is optionally substituted with 1-5 halogens;

R$^5$ and R$^6$ are each independently selected from the group consisting of H, halogen, —C$_1$-C$_5$ alkyl, —OC$_1$-C$_5$ alkyl, —C$_2$-C$_5$ alkenyl, —OC$_2$-C$_5$ alkenyl, C$_3$-C$_6$ cycloalkyl, —(CH$_2$)$_m$phenyl, and —O(CH$_2$)$_m$phenyl, wherein —C$_1$-C$_5$ alkyl, —OC$_1$-C$_5$ alkyl, —C$_2$-C$_5$ alkenyl, and —OC$_2$-C$_5$ alkenyl are optionally substituted with 1-5 halogens, and wherein C$_{3-6}$ cycloalkyl and the phenyl of —(CH$_2$)$_m$phenyl and —O(CH$_2$)$_m$phenyl are optionally substituted with 1-5 groups independently selected from halogen, C$_1$-C$_3$ alkyl and —OC$_1$-C$_3$ alkyl, said C$_1$-C$_3$ alkyl and —OC$_1$-C$_3$ alkyl being optionally substituted with 1-3 halogens; or alternatively R$^5$ and R$^6$ may be joined to form a C$_3$-C$_6$ cycloalkyl group, said C$_3$-C$_6$ cycloalkyl group optionally being substituted with 1-3 halogens;

R$^7$ is selected from the group consisting of H and —C$_1$-C$_6$ alkyl, wherein C$_1$-C$_6$ alkyl is optionally substituted with 1-5 halogens;

m in each instance is an integer from 0-2;
n in each instance is an integer from 0-2;
p is an integer from 0 to 3; and
q is an integer from 0-3.

DETAILED DESCRIPTION OF THE INVENTION

The invention is described in connection with the following definitions.

"Ac" is acetyl, which is CH$_3$C(O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring system having a specified number of rings and a specified ring size (e.g. monocyclic 3-7-membered ring). A cycloalkyl can be fused to an aryl group. Examples of cycloalkyl include cyclopropyl, cyclopentyl, cyclohexyl, cycloheptyl, and the like. A cycloalkyl fused to an aromatic ring can be for example an indane ring or a tetrahydronaphthalene ring.

A cycloalkylidene group is a divalent cycloalkane radical in which both attachments are at the same carbon. For example, the cyclopropyl group of 1,1-dimethylcyclopropane is a cyclopropylidene group.

"Aryl" (and "arylene") when used to describe a substituent or group in a structure means an aromatic carbocyclic ring system having a specified number of rings and a specified ring size, as for example, a monocyclic or bicyclic aromatic system having 5-7-membered rings. Typical aryl groups include phenyl and naphthyl. Phenyl is generally the most preferred aromatic group. An aryl group can be fused to a cycloalkyl or heterocycle. "Heterocyclic" and "heterocycle" means a fully or partially saturated ring system containing a specified number of heteroatoms, a specified number of rings, and a specified ring size (e.g., heterocyclic monocyclic rings having 1-3 heteroatoms independently selected from N, S and O, each of said rings having 5-7 atoms). Examples of an aryl ring fused to heterocyclic groups include 2,3-dihydrobenzofuranyl, dihydrobenzopyranyl, and the like. Examples of monocyclic heterocycles include tetrahydrofuran, piperazine, and morpholine.

"Fused" has the meaning commonly used in organic chemistry. Two carbocyclic and/or heterocyclic rings are fused if they share a common side, as exemplified in the definitions of benzoheteroaryl and aryl.

"Heteroaryl" or "heterocyclic aromatic" means a mono- or polycyclic aromatic ring system containing a specified number of heteroatoms, a specified number of rings, and a specified ring size (e.g. a monocyclic ring having 1-3 heteroatoms independently selected from N, O and S, including —S(O)— and —S(O)$_2$—, with each ring containing 5 to 6 atoms). Examples of monocyclic heteroaryls include pyrrolyl, isoxazolyl, isothiazolyl, pyrazolyl, pyridinyl, oxazolyl, oxadiazolyl, thiadiazolyl, thiazolyl, imidazolyl, triazolyl, tetrazolyl, furanyl, triazinyl, thienyl, pyrimidinyl, pyridazinyl, and pyrazinyl.

"Benzoheteroaryl" or "benzoheteroaromatic" refers to bicyclic rings comprising a phenyl ring fused to a monocyclic heteroaromatic ring. Examples of benzoheteroaryl include benzisoxazolyl, benzoxazolyl, benzisothiazolyl, benzothiazolyl, benzimidazolyl, benzofuryl, benzothienyl (including S-oxide and dioxide), quinolyl, isoquinolyl, indazolyl, indolyl, and the like.

"Halogen" includes fluorine, chlorine, bromine and iodine.

"Me" represents methyl.

Note that "C" in ring A of formula I represents a carbon atom.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

The compounds used in the present invention are PPAR-gamma agonists and partial agonists. The compounds are potent ligands of the PPAR gamma nuclear receptor. The class of compounds includes many compounds that are PPARγ partial agonists, but also may include PPARγ full agonists and/or PPARγ antagonists. Some compounds may also have PPARα activity in addition to PPARγ activity. The compounds are useful in a once weekly dosing regimen for the treatment and control of hyperglycemia and insulin resistance. The compounds are efficacious in the treatment of non-insulin dependent diabetes mellitus (NIDDM) in human and other mammalian patients, particularly in the treatment of hyperglycemia, and in the treatment of conditions associated with NIDDM, including hyperlipidemia, dyslipidemia, obesity, hypercholesterolemia, hypertriglyceridemia, atherosclerosis, vascular restenosis, inflammatory conditions, and other PPAR mediated diseases, disorders and conditions.

The compounds are useful for the treatment of pre-diabetes, and are also useful for the treatment of type 1 diabetes.

The compounds may also be useful in the treatment of one or more lipid disorders, including mixed or diabetic dyslipidemia, isolated hypercholesterolemia, which may be manifested by elevations in LDL-C and/or non-HDL-C, hyper-apoB liproteinemia, hypertriglyceridemia, an increase in triglyceride-rich-lipoproteins, and low HDL cholesterol concentrations. They may also be useful in the treatment or amelioration of atherosclerosis, obesity, vascular restenosis, inflammatory conditions, psoriasis, polycystic ovary syndrome, and other PPAR mediated diseases, disorders and conditions.

The invention has numerous embodiments, as set forth below.

In one subset of the invention in which the compound is administered once weekly, Ring A together with the phenyl ring to which ring A is fused forms a naphthalene ring or a benzoheteroaromatic ring selected from the group consisting of quinolyl, isoquinolyl, benzisoxazolyl, indolyl, indazolyl, benzofuryl, and benzothienyl.

In other subsets of the method described herein, in the compound of Formula I:

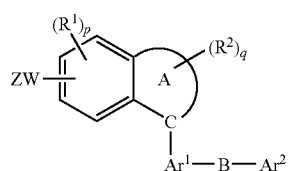

or a pharmaceutically acceptable salt or solvate thereof wherein:

Ring A together with the phenyl ring to which ring A is fused forms a naphthalene ring or a benzoheteroaromatic ring selected from the group consisting of quinolyl, benzisoxazolyl, indolyl, indazolyl, benzofuryl, and benzothienyl;

$Ar^1$ is selected from the group consisting of phenyl, pyrimidinyl, and pyridinyl, and $Ar^2$ is selected from the group consisting of phenyl and pyridinyl, where $Ar^1$ and $Ar^2$ are each optionally substituted with 1-4 substituent groups independently selected from halogen, —$C_1$-$C_4$ alkyl, —$OC_1$-$C_4$ alkyl, —$S(O)_n C_1$-$C_4$ alkyl, —$NO_2$, and —CN, wherein —$C_1$-$C_4$ alkyl, —$OC_1$-$C_4$ alkyl, and —$S(O)_n C_1$-$C_4$ alkyl are each optionally substituted with 1-3 halogens;

B is selected from —O— and —C(=O)—;

—WZ is —O—$C(R^5)(R^6)$—$CO_2 R^7$;

$R^1$ and $R^2$ are each independently selected from the group consisting of halogen, —OH, —CN, —$NO_2$, —$C_1$-$C_3$ alkyl, —$OC_1$-$C_3$ alkyl, —$S(O)_2 CH_3$, and —$S(O)_2 CF_3$, wherein —$C_1$-$C_3$ alkyl and —$OC_1$-$C_3$ alkyl are optionally substituted with 1-3 halogens;

$R^5$ and $R^6$ are each independently selected from the group consisting of H, halogen, and —$C_1$-$C_4$ alkyl, wherein —$C_1$-$C_4$ alkyl is optionally substituted with 1-5 halogens;

$R^7$ is selected from the group consisting of H and $C_1$-$C_6$ alkyl, wherein $C_1$-$C_6$ alkyl is optionally substituted with 1-5 halogens;

n is an integer from 0-2;

p is an integer from 0 to 2; and q is an integer from 0-2.

In another subset, in the compound used in the present invention, Ring A together with the phenyl ring to which ring A is fused forms a naphthalene ring or a benzoheteroaromatic ring selected from the group consisting of benzisoxazolyl, indolyl, indazolyl, benzofuryl, and benzothienyl.

In another subset, in the compound used in the present invention, $Ar^1$ and $Ar^2$ are each independently selected from the group consisting of phenyl and pyridinyl, which are each optionally substituted with 1-4 substituent groups independently selected from halogen, —$C_1$-$C_4$ alkyl, —$OC_1$-$C_4$ alkyl, —$S(O)_n C_1$-$C_4$ alkyl, —$NO_2$, and —CN, wherein —$C_1$-$C_4$ alkyl, —$OC_1$-$C_4$ alkyl, and —$S(O)_n C_1$-$C_4$ alkyl are each optionally substituted with 1-3 halogens.

In another subset, in the compound used in the present invention, Ring A together with the phenyl ring to which ring A is fused forms a naphthalene ring or a benzoheteroaromatic ring selected from the group consisting of benzisoxazolyl, indazolyl, and benzofuryl.

In another subset, in the compound used in the present invention, $Ar^1$ is selected from the group consisting of phenyl and pyridinyl, and is optionally substituted with 1-2 groups which are independently selected from $C_1$-$C_4$ alkyl, wherein $C_1$-$C_4$ alkyl is optionally substituted with 1-3 halogens.

In another subset, in the compound used in the present invention, $Ar^2$ is phenyl, which is optionally substituted with 1-2 substituent groups independently selected from halogen, —CN, —$C_1$-$C_3$ alkyl, and —$OC_1$-$C_3$ alkyl, wherein —$C_1$-$C_3$ alkyl and —$OC_1$-$C_3$ alkyl are optionally substituted with 1-3 halogens.

In another subset, in the compound used in the present invention, B is —O—. In subsets of compounds of Formula I, B is —C(=O)—. In subsets of compounds of Formula I, B is —C(=O)— or —O—.

In another subset, in the compound used in the present invention, —WZ is —O—$C(R^5)(R^6)$—$CO_2 H$.

In another subset, in the compound used in the present invention, each $R^1$ is independently selected from the group consisting of halogen, —$C_1$-$C_3$ alkyl, and —OH, wherein —$C_1$-$C_3$ alkyl is optionally substituted with 1-3 halogens.

In another subset, in the compound used in the present invention, each $R^2$ is independently selected from the group consisting of —C$_1$-C$_3$ alkyl, —S(O)$_2$CH$_3$, and —S(O)$_2$CF$_3$, wherein —C$_1$-C$_3$ alkyl is optionally substituted with 1-3 halogens.

In another subset, in the compound used in the present invention, R$^5$ and R$^6$ are each H or —C$_1$-C$_3$ alkyl.

In another subset, in the compound used in the present invention, q and p are each independently integers from 0-2. In another subset, in the compound used in the present invention, q is an integer which is 0 or 1. In another subset, in the compound used in the present invention, p is an integer which is 0 or 1.

A preferred aspect of the invention relates to the administration on a once weekly basis of a compound of Formula II:

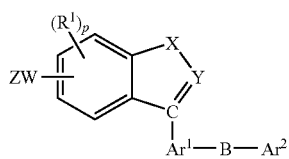

II or a pharmaceutically acceptable salt or solvate thereof wherein: X-Y is —O—N═, —N(R$^2$)—N═, —O—C(R$^2$)═, —S—C(R$^2$)═, or —N(R$^2$)—(CR$^2$)═, and the other substituent groups are as defined previously.

In many subsets of the present invention, the compound administered on a weekly basis is of Formula II wherein:

Ar$^1$ is selected from the group consisting of phenyl, pyrimidinyl, and pyridinyl, and is optionally substituted with 1-2 groups which are independently selected from C$_1$-C$_4$ alkyl, wherein C$_1$-C$_4$ alkyl is optionally substituted with 1-3 halogens;

Ar$^2$ is phenyl, which is optionally substituted with 1-2 substituent groups independently selected from halogen, —CN, —C$_1$-C$_3$ alkyl, and —OC$_1$-C$_3$ alkyl, wherein —C$_1$-C$_3$ alkyl and —OC$_1$-C$_3$ alkyl are optionally substituted with 1-3 halogens;

B is selected from —O— and —C(═O)—;

—WZ is —O—C(R$^5$)(R$^6$)—CO$_2$R$^7$;

each R$^1$ is independently selected from the group consisting of halogen, —C$_1$-C$_3$ alkyl, —OC$_1$-C$_3$ alkyl, and —OH, wherein —C$_1$-C$_3$ alkyl and —OC$_1$-C$_3$ alkyl are optionally substituted with 1-3 halogens;

each R$^2$ is independently selected from the group consisting of H, —C$_1$-C$_3$ alkyl, —S(O)$_2$CH$_3$, and —S(O)$_2$CF$_3$, wherein —C$_1$-C$_3$ alkyl is optionally substituted with 1-3 halogens;

R$^5$ and R$^6$ are each independently selected from the group consisting of H and C$_1$-C$_3$ alkyl, wherein —C$_1$-C$_3$ alkyl is optionally substituted with 1-5 halogens;

R$^7$ is H or —C$_1$-C$_5$ alkyl; and p is an integer from 0-2.

In other subsets, in the compounds used in the present invention, Ar$^1$ is selected from the group consisting of phenyl and pyridinyl, and is optionally substituted with 1-2 groups which are independently selected from C$_1$-C$_4$ alkyl, wherein C$_1$-C$_4$ alkyl is optionally substituted with 1-3 halogens.

In another subset of the invention, the compound administered on a weekly basis is of formula III:

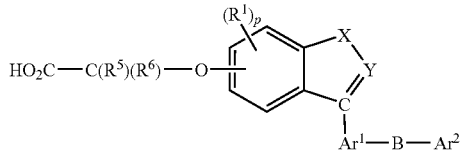

III wherein: X-Y is selected from the group consisting of —O—N═, —N(R$^2$)—N═, and —O—C(R$^2$)═;

Ar$^1$ is selected from the group consisting of phenyl, pyrimidinyl, and pyridinyl, wherein Ar$^1$ is optionally substituted with a —C$_2$-C$_4$ alkyl group, which is optionally substituted with 1-3 F;

each R$^1$ is independently selected from the group consisting of halogen, CH$_3$, —CF$_3$, —OH, —OCH$_3$, and —OCF$_3$;

R$^2$ is selected from the group consisting of H, —C$_1$-C$_3$ alkyl, —CF$_3$, —S(O)$_2$CH$_3$, and —S(O)$_2$CF$_3$;

R$^5$ is H or —C$_1$-C$_3$ alkyl; and

R$^6$ is —C$_1$-C$_3$ alkyl.

In another subset of the invention, the compound administered on a weekly basis if of formula III wherein: Ar$^1$ is phenyl or pyridinyl, wherein Ar$^1$ is optionally substituted with a —C$_2$-C$_4$ alkyl group, which is optionally substituted with 1-3 F; or is substituted as previously defined.

In another subset of the present invention, the compound administered on a weekly basis is of formula I, II or III, wherein: Ar$^1$ is selected from the group consisting of phenyl, pyrimidinyl, and pyridinyl, wherein pyridinyl is connected through the 3-position to the C-atom of the ring A to which Ar$^1$ is connected, pyrimidinyl is connected through the 5-position to the C-atom of the ring A to which Ar$^1$ is connected, and Ar$^1$ is substituted with one —C$_2$-C$_4$ alkyl substituent.

In another subset of the invention, the compound administered on a weekly basis is of formula I, II or III, wherein: Ar$^2$ is phenyl, which is optionally substituted with 1-2 substituent groups independently selected from halogen, —CN, —C$_1$-C$_2$ alkyl, —CF$_3$, —OCH$_3$, and —OCF$_3$.

In another subset of the invention, the compound administered on a weekly basis is of formula I, II or III wherein: B is —O—.

In other subsets of the invention, the compounds that are administered on a weekly basis are of formula I, II or III, wherein each R$^1$ is independently selected from the group consisting of halogen, —CH$_3$, —CF$_3$, and —OH.

In other subsets of the invention, the compounds administered on a weekly basis are of formula I, II or III, wherein R$^2$ is selected from the group consisting of H, —CH$_3$, —CF$_3$, —S(O)$_2$CH$_3$, and —S(O)$_2$CF$_3$.

In another subset of the invention, the compound administered on a weekly basis is of formula I, II or III, wherein R$^5$ is H or —CH$_3$.

In another subset of the invention, the compound administered on a weekly basis is of formula I, II or III, wherein R$^6$ is —C$_1$-C$_3$ alkyl.

In another subset of the invention, the compound administered on a weekly basis is of formula I, II or III, wherein: Ar$^1$ is selected from the group consisting of phenyl and pyridinyl, wherein pyridinyl is connected at the 3-position to the C-atom of the ring A to which Ar$^1$ is connected, and Ar$^1$ is substituted with one —C$_2$-C$_4$ alkyl substituent which is optionally substituted with 1-3 F; or in other subsets, Ar$^1$ is substituted with one —C$_2$-C$_4$ alkyl substituent which is not substituted further; or in other subsets, Ar$^1$ is substituted with one group n-propyl.

In another subset of the invention, the compound administered on a weekly basis is of Formula IV:

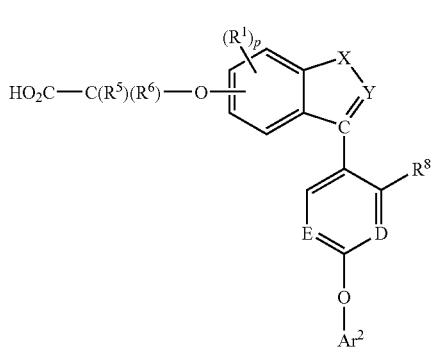

wherein: D and E are each independently selected from —CH= and —N=; and $R^8$ is —$C_2$-$C_4$ alkyl, which is optionally substituted with 1-3 F. Other substituents may have any of the definitions described previously.

In another subset of the invention, the compound administered on a weekly basis is of formula IV wherein: $R^8$ is —$C_2$-$C_4$ alkyl, which is not further substituted. In other subsets, $R^8$ is n-propyl.

In another subset of the invention, the compound administered on a weekly basis is of Formula V:

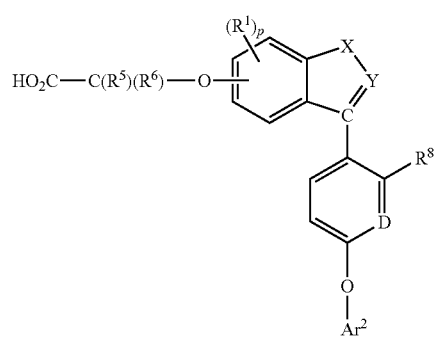

where D is —CH= or —N=; and $R^8$ is —C—$C_4$ alkyl, which is optionally substituted with 1-3 F.

Other subsets comprise compounds having Formula VI below, including pharmaceutically acceptable salts thereof:

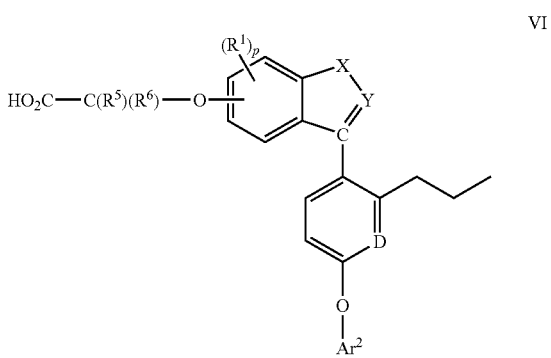

In another subset of the invention, the compound administered on a weekly basis is of formula VI wherein:

D is —CH= or —N=;

$R^2$ is H, —$CH_3$, or —$S(O)_2CH_3$; and Note: $R^2$ not present in VI $R^6$ is $C_1$-$C_2$ alkyl.

In another subset of the invention, the compound administered on a weekly basis is a compound of Formula IV, V or VI wherein: X-Y is —O—N= and D is —CH=.

In another subset of the invention, the compound that is administered on a weekly basis is a compound of Formula IV, V or VI, wherein: X-Y is —O—N=, and D is —N=, In another aspect of the invention, a compound of Formula I, II, III, IV, V or VI, including pharmaceutically acceptable salts of these compounds, prodrugs of these compounds, is administered to a patient on a weekly basis in the form of a pharmaceutical composition which is comprised of the compound described above in combination with a pharmaceutically acceptable carrier. Disclosure herein relating to compounds of Formula I or the compound of Formula I also is meant to include all subsets of Formula I, including Formula II, III, IV, V and VI, as well as specific compounds disclosed herein.

Examples of compounds that are administered on a weekly basis are disclosed below. The specific compounds used also include pharmaceutically acceptable salts thereof.

TABLE 1

| Example | Chemical Name | Structure |
|---|---|---|
| 1 | (2S)-2-({3-[4-(4-chlorophenoxy)-2-propylphenyl]-1-benzofuran-5-yl}oxy)propanoic acid | 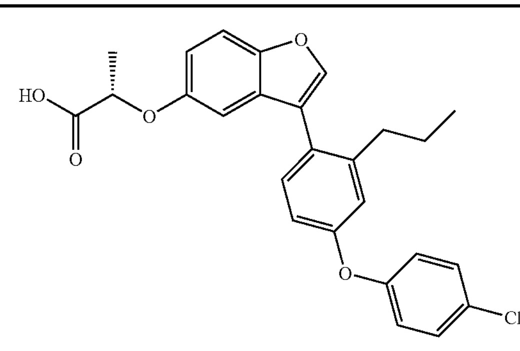 |

TABLE 1-continued

| Example | Chemical Name | Structure |
|---|---|---|
| 2 | (2S)-2-({6-chloro-3-[4-(4-chlorophenoxy)-2-propylphenyl]-1-benzofuran-5-yl}oxy)propanoic acid | 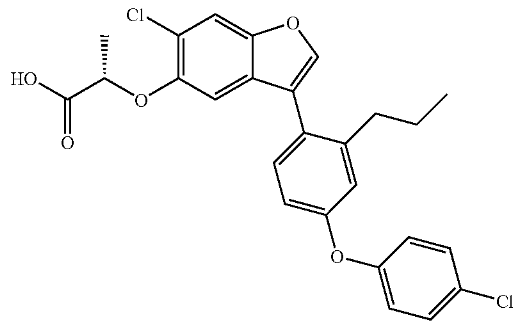 |
| 3 | (2S)-2-({3-[4-(4-chlorophenoxy)-2-propylphenyl]-1,2-benzisoxazol-5-yl}oxy)propanoic acid | 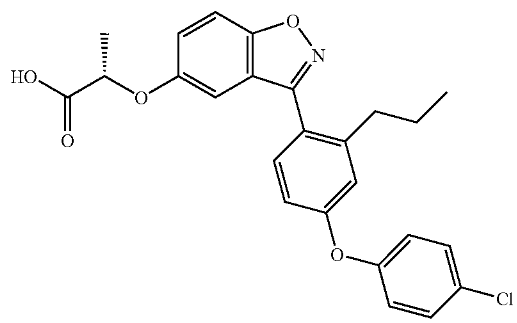 |
| 4 | (2S)-2-({4-chloro-3-[4-(4-chlorophenoxy)-2-propylphenyl]-1,2-benzisoxazol-5-yl}oxy)propanoic acid | 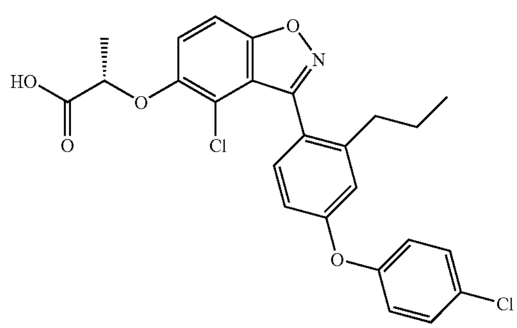 |
| 5 | (2R)-2-({6-chloro-3-[4-(4-chlorophenoxy)-2-propylphenyl]-1,2-benzisoxazol-5-yl}oxy)propanoic acid | 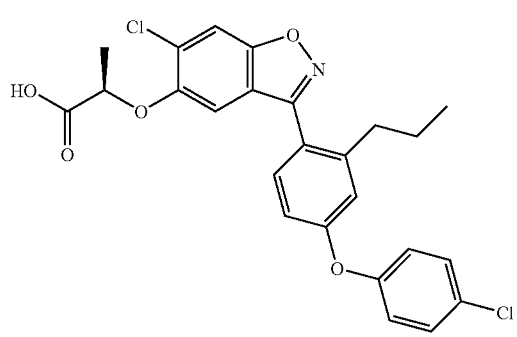 |

TABLE 1-continued
| Example | Chemical Name | Structure |
|---|---|---|
| 6 | (2S)-2-({6-chloro-3-[4-(4-chlorophenoxy)-2-propylphenyl]-1,2-benzisoxazol-5-yl}oxy)propanoic acid | 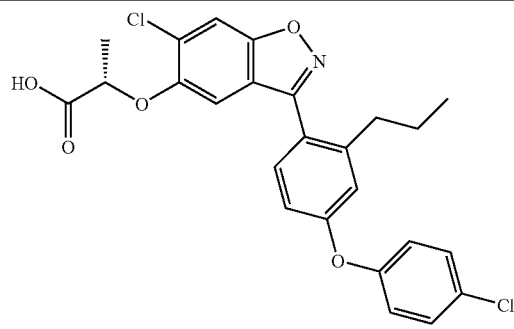 |
| 7 | (2S)-2-({6-chloro-3-[4-(4-methylphenoxy)-2-propylphenyl]-1,2-benzisoxazol-5-yl}oxy)propanoic acid | 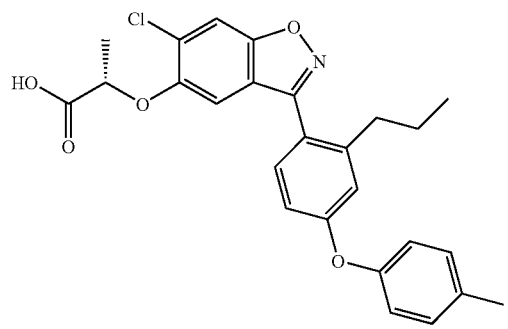 |
| 8 | (2S)-2-({6-chloro-3-[4-(4-ethylphenoxy)-2-propylphenyl]-1,2-benzisoxazol-5-yl}oxy)propanoic acid | 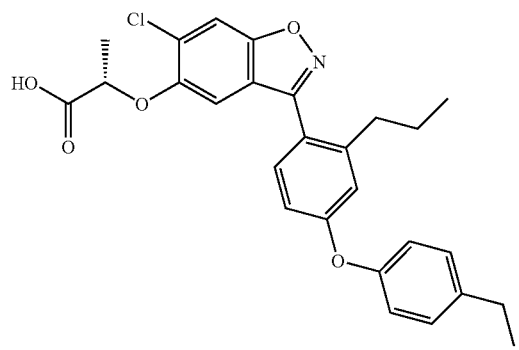 |
| 9 | (2S)-2-[(6-chloro-3-{2-propyl-4-[4-(trifluoromethoxy)phenoxy]phenyl}-1,2-benzisoxazol-5-yl)oxy]propanoic acid | 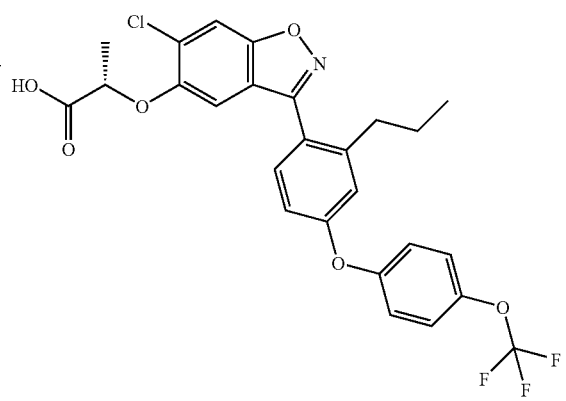 |

TABLE 1-continued

| Example | Chemical Name | Structure |
|---|---|---|
| 10 | (2S)-2-({6-chloro-3-[4-(3-chlorophenoxy)-2-propylphenyl]-1,2-benzisoxazol-5-yl}oxy)propanoic acid | 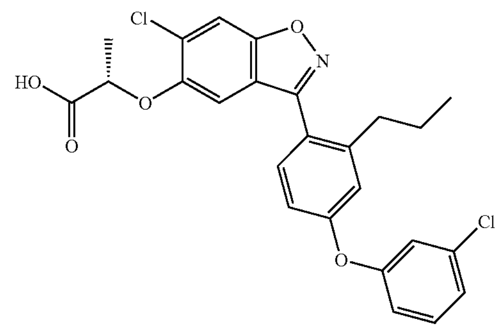 |
| 11 | (2S)-2-({6-chloro-3-[4-(3-chloro-4-methylphenoxy)-2-propylphenyl]-1,2-benzisoxazol-5-yl}oxy)propanoic acid | 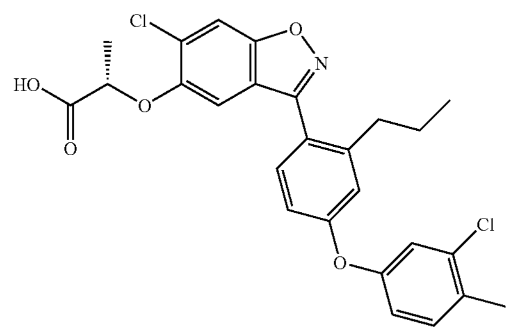 |
| 12 | ({6-chloro-3-[6-(4-chlorophenoxy)-2-propylpyridin-3-yl]-1,2-benzisoxazol-5-yl}oxy)acetic acid | 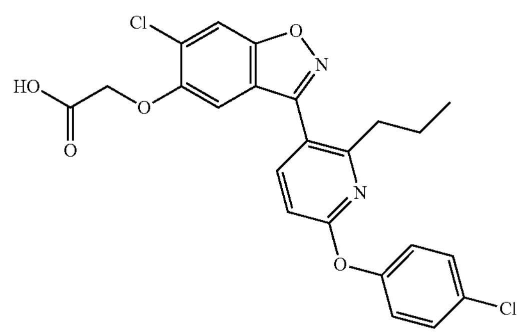 |
| 13 | 2-({6-chloro-3-[6-(4-chlorophenoxy)-2-propylpyridin-3-yl]-1,2-benzisoxazol-5-yl}oxy)butanoic acid | 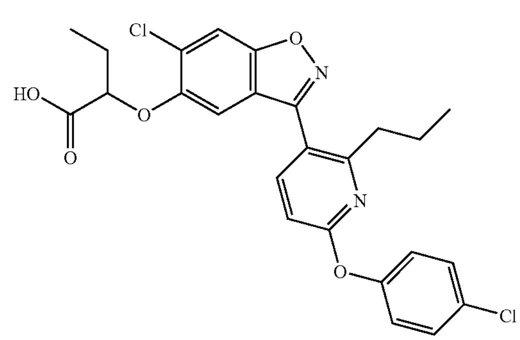 |

TABLE 1-continued

| Example | Chemical Name | Structure |
|---|---|---|
| 14 | (2S)-2-({6-chloro-3-[6-(4-chlorophenoxy)-2-propylpyridin-3-yl]-1,2-benzisoxazol-5-yl}oxy)propanoic acid | 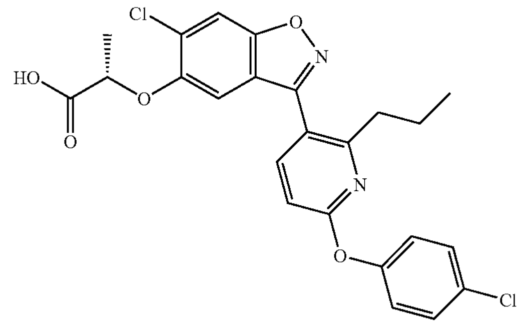 |
| 15 | (2S)-2-({6-chloro-3-[6-(4-fluorophenoxy)-2-propylpyridin-3-yl]-1,2-benzisoxazol-5-yl}oxy)propanoic acid | 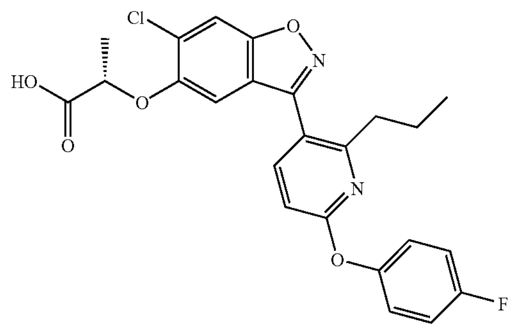 |
| 16 | (2S)-2-{[6-chloro-3-(6-phenoxy-2-propylpyridin-3-yl)-1,2-benzisoxazol-5-yl]oxy}propanoic acid | 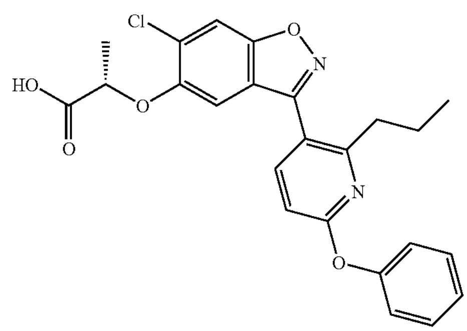 |
| 17 | (2R)-2-({6-chloro-3-[6-(4-chlorophenoxy)-2-propylpyridin-3-yl]-1,2-benzisoxazol-5-yl}oxy)propanoic acid | 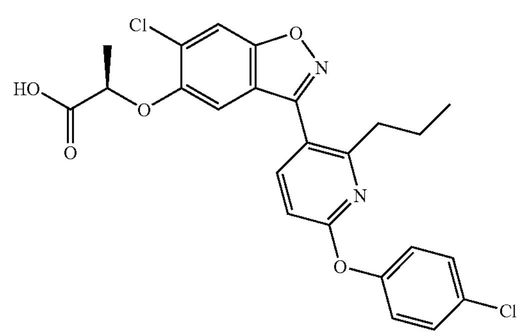 |

TABLE 1-continued

| Example | Chemical Name | Structure |
|---|---|---|
| 18 | (2S)-2-({6-chloro-3-[6-(4-cyanophenoxy)-2-propylpyridin-3-yl]-1,2-benzisoxazol-5-yl}oxy)propanoic acid | 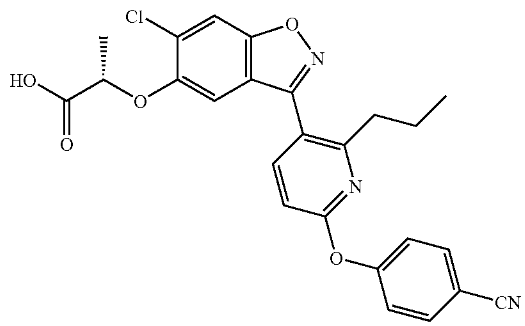 |
| 19 | (2S)-2-({6-chloro-3-[6-(4-chlorophenoxy)pyridin-3-yl]-1,2-benzisoxazol-5-yl}oxy)propanoic acid | 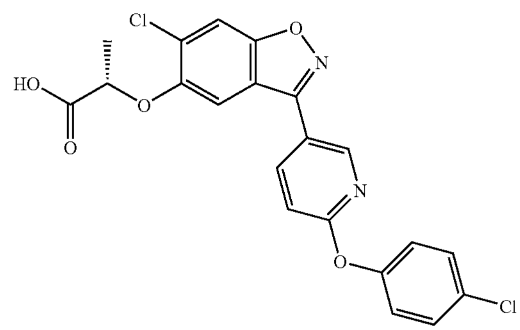 |
| 20 | (2S)-2-({6-chloro-3-[6-(4-chlorophenoxy)-2-propylpyridin-3-yl]-1-methyl-1H-indazol-5-yl}oxy)propanoic acid | 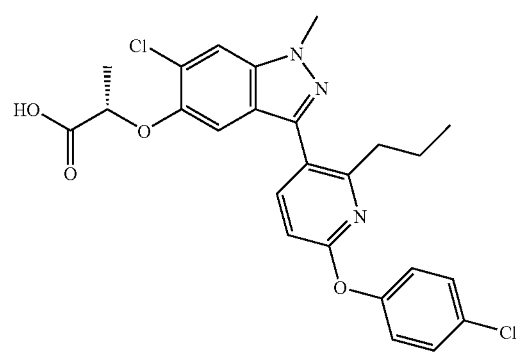 |
| 21 | (2S)-2-({6-chloro-3-[6-(4-chlorophenoxy)-2-propylpyridin-3-yl]-1H-indazol-5-yl}oxy)propanoic acid | 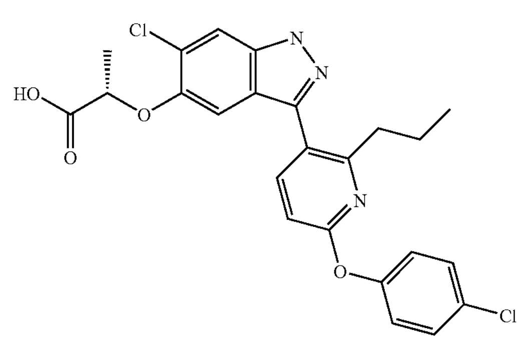 |

TABLE 1-continued

| Example | Chemical Name | Structure |
|---|---|---|
| 22 | (2S)-2-{[6-chloro-3-[6-(4-chlorophenoxy)-2-propylpyridin-3-yl]-1-(methylsulfonyl)-1H-indazol-5-yl]oxy}propanoic acid | 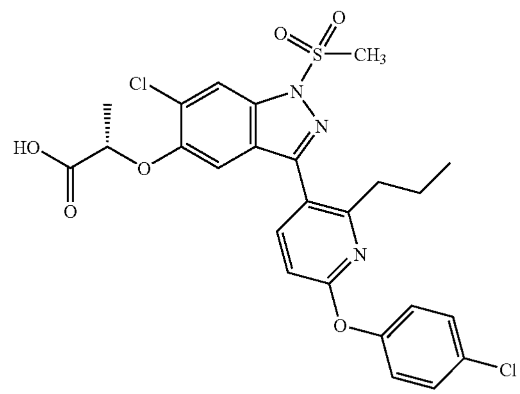 |
| 23 | (2S)-2-({8-[4-(4-fluorobenzoyl)phenyl]-2-naphthyl}oxy)propanoic acid | 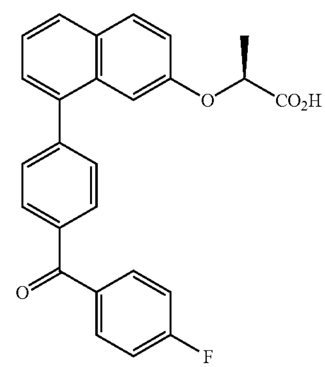 |
| 24 | ({8-[2-(4-chlorophenoxy)pyrimidin-5-yl]-2-naphthyl}oxy)acetic acid | 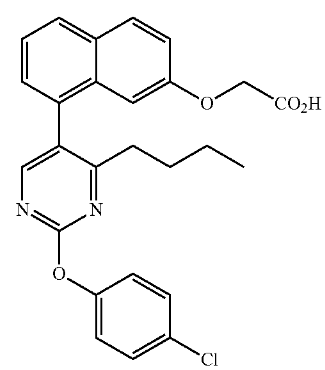 |

Table 2 provides additional specific compounds, including pharmaceutically acceptably salts thereof, that can be readily made using the procedures in this application by a practitioner in the field of synthetic organic chemistry.

TABLE 2

| Example | Chemical Name | Structure |
|---|---|---|
| 2-1 | 2-({8-[4-(4-fluorobenzoyl)phenyl]-2-naphthyl}oxy)-2-methylpropanoic acid | 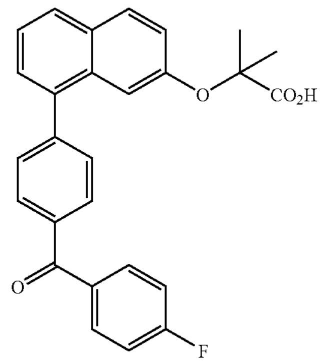 |
| 2-2 | 2-({8-[4-(4-methoxybenzoyl)phenyl]-2-naphthyl}oxy)-2-methylpropanoic acid | 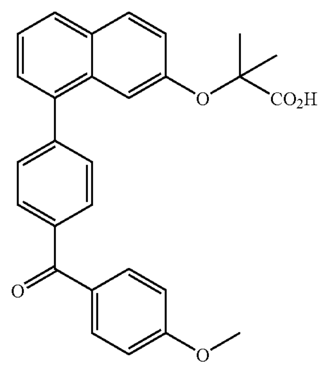 |
| 2-3 | (2R)-2-({8-[4-(4-fluorophenoxy)phenyl]-2-naphthyl}oxy)propanoic acid | 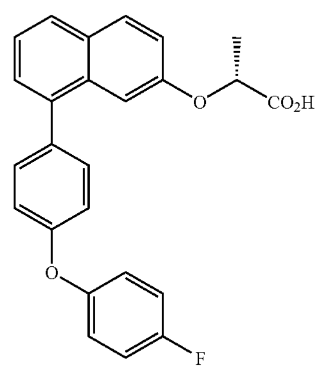 |
| 2-4 | (2S)-2-({8-[4-(4-fluorophenoxy)phenyl]-2-naphthyl}oxy)propanoic acid | 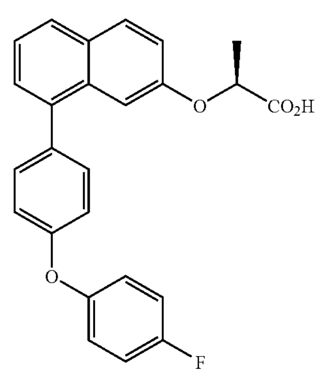 |

TABLE 2-continued

| Example | Chemical Name | Structure |
|---|---|---|
| 2-5 | 2-({8-[4-(4-fluorophenoxy)phenyl]-2-naphthyl}oxy)-2-methylpropanoic acid | 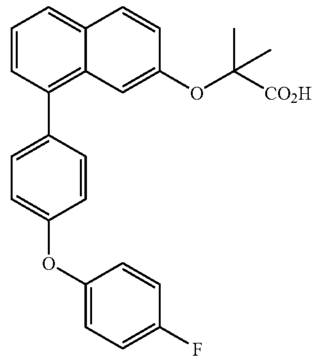 |
| 2-6 | 2-({8-[4-(4-fluorophenoxy)-3-propylphenyl]-2-naphthyl}oxy)-2-methylpropanoic acid | 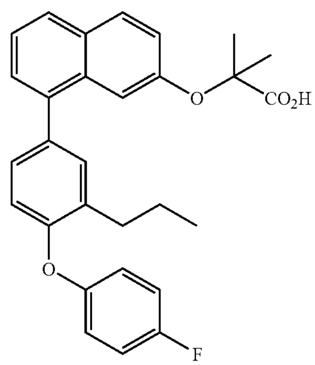 |
| 2-7 | (2S)-2-({8-[4-(4-fluorophenoxy)-3-propylphenyl]-2-naphthyl}oxy)propanoic acid | 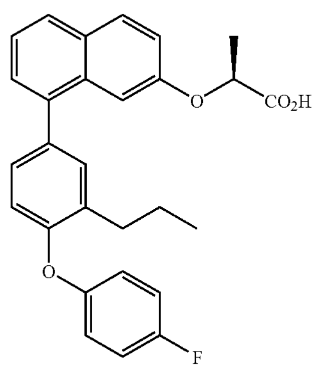 |
| 2-8 | 2-({3-[4-4-chlorophenoxy]-2-propylphenyl}-1,2-benzisoxazol-5-yl)oxy)propanoic acid | 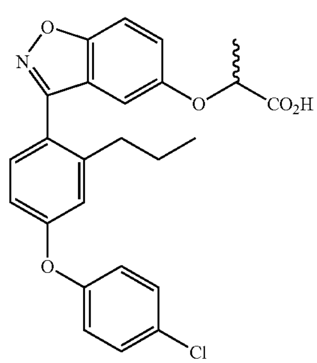 |

TABLE 2-continued

| Example | Chemical Name | Structure |
|---|---|---|
| 2-9 | (2S)-2-({6-chloro-3-[4-(4-fluorophenoxy)-2-propylphenyl]-1,2-benzisoxazol-5-yl}oxy)propanoic acid | 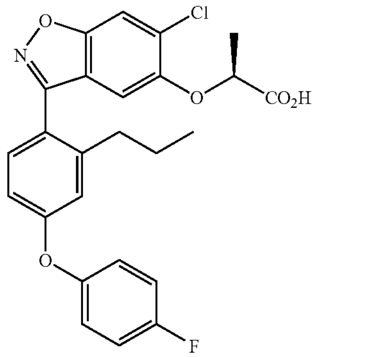 |
| 2-10 | (2S)-2-({6-chloro-3-[6-(4-chlorophenoxy)-2-propylpyridin-3-yl]-4-iodo-1,2-benzisoxazol-5-yl}oxy)propanoic acid | 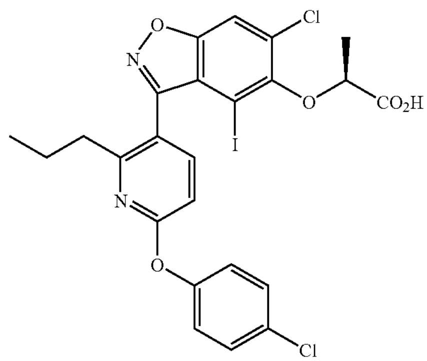 |

The compounds of this invention can be used in pharmaceutical compositions comprising the compound or a pharmaceutically acceptable salt thereof and a pharmaceutically acceptable carrier, optionally with one or more additional other active pharmaceutical ingredients. The compounds of this invention can be used in pharmaceutical compositions in which a compound of Formula I, or a pharmaceutically acceptable salt thereof, is the only active ingredient.

The compounds of the invention and pharmaceutically acceptable salts thereof are suitable for use in the manufacture of medicaments for the treatment of type 2 diabetes mellitus in a human or other mammalian patient, and in the manufacture of medicaments for other diseases described below that are treated by the compounds. The preferred patient is human.

The compounds as defined above may be used in any of the following methods to treat or control diseases, as well as methods to treat other diseases not listed below, in a mammalian patient, especially a human, by administering to the patient once weekly a therapeutically effective amount for the specific disease (or diseases) of a compound of Formula I:
  (1) insulin dependent (type 1 diabetes) and non-insulin dependent diabetes mellitus (type 2 diabetes);
  (2) pre-diabetes (insulin resistance);
  (3) hyperglycemia;
  (4) metabolic syndrome;
  (5) obesity;
  (6) hypercholesterolemia;
  (7) hypertriglyceridemia; and/or
  (8) one or more lipid disorders, including mixed or diabetic dyslipidemia, low HDL cholesterol, high LDL cholesterol, hyperlipidemia, hypercholesterolemia, and hypertriglyceridemia.

The compounds may also be used in a method for reducing the risks of adverse sequelae associated with metabolic syndrome in a human or other mammalian patient in need of such treatment which comprises administering to the patient once weekly a therapeutically effective amount of a compound of Formula I, or a pharmaceutically acceptable salt thereof.

The compounds may also be used in a method for treating atherosclerosis, for reducing the risk of developing atherosclerosis, for delaying the onset of atherosclerosis, and/or reducing the risk of sequelae of atherosclerosis in a human or other mammalian patient in need of such treatment or at risk of developing atherosclerosis or sequelae of atherosclerosis, which comprises administering to the patient once weekly a therapeutically effective amount of a compound of Formula I. Sequelae of atherosclerosis include for example angina, claudication, heart attack, stroke, etc.

The compounds are especially useful in the treatment of the following diseases, by administering once weekly a therapeutically effective amount (for the specific disease) of the compound, or a pharmaceutically acceptable salt thereof, to a patient in need of treatment:
  (1) type 2 diabetes, and especially hyperglycemia resulting from type 2 diabetes;
  (2) metabolic syndrome;
  (3) obesity; and
  (4) hypercholesterolemia.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to comprehend all such isomeric forms of the compounds of Formula I.

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using starting materials and/or reagents that are optically pure and/or have a known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic or has a basic group in the structure, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Preferred acids include citric, hydrobromic, hydrochloric, maleic, phosphoric, sulfuric, tartaric, toluenesulfonic (tosylate), methanesulfonic (mesylate) and benzenesulfonic (besylate) acid salts, most preferably the benzenesulfonic, toluenesulfonic and methanesulfonic acid salts. In some instances the compounds of the invention may be present in zwitterionic forms.

It will be understood that, as used herein, references to the compounds of Formula I are meant to also include the pharmaceutically acceptable salts.

Metabolites—Prodrugs

Metabolites of the claimed compounds which themselves fall within the scope of the claimed invention are also compounds of the current invention. Prodrugs, which are compounds that are converted to the claimed compounds as they are being administered to a patient or after they have been administered to a patient, also may be considered compounds of this invention.

Utilities

Compounds of the present invention are potent ligands having agonist, partial agonist or antagonist activity on one or more of the various peroxisome proliferator activated receptor subtypes, particularly PPARγ. The compounds may also be ligands or agonists, partial agonists or antagonists of the PPARα subtype as well as the PPARγ subtype, resulting in mixed PPARα/γ agonism. Some compounds may also be PPAR ligands and have PPAR activity in addition to their other PPAR activity. The compounds of this invention are useful in treating or controlling diseases, disorders or conditions which are mediated by one or more ligands of the individual PPAR subtypes (eg. γ or α) or a combination of PPAR subtypes (e.g. α/γ). One aspect of the present invention provides a method for the treatment and control of diseases that can be mediated by administration of a PPAR agonist or partial agonist, particularly a PPAR γ agonist or partial agonist, such as type 2 diabetes. One aspect of the present invention provides a method for the treatment and control of diseases, disorders, or conditions which are mediated by one or more PPAR subtypes in a mammal which comprises administering to such a mammal a therapeutically effective amount of a compound of Formula I, or a pharmaceutically acceptable salt thereof. Compounds of the present invention may be useful in treating or controlling many PPAR mediated diseases and conditions, including, but not limited to, (1) diabetes mellitus, and especially non-insulin dependent on type 2 diabetes mellitus (NIDDM), (2) hyperglycemia, (3) low glucose tolerance, (4) pre-diabetes or insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, such as Alzheimer's disease, multiple sclerosis, Parkinson's disease and the like; (21) retinopathy, (22) psoriasis, (23) metabolic syndrome, (24) ovarian hyperandrogenism (polycystic ovarian syndrome), and other disorders where insulin resistance is a component. They may also have utility in treating high blood pressure, neoplastic conditions, adipose cell tumors, adipose cell carcinomas, such as liposarcoma, prostate cancer and other cancers, including gastric, breast, bladder and colon cancers and angiogenesis.

The compounds can also be used for the treatment of respiratory conditions, such as asthma.

The present compounds can be used to lower glucose, lipids, and insulin in non-diabetic patients who have impaired glucose tolerance and/or are in a pre-diabetic condition by the administration to a patient in need of treatment a therapeutically effective amount of a compound having Formula I, or Pharmaceutically acceptable salt thereof.

The present compounds can be used to treat obesity in a patient in need of such treatment by administering to the patient a therapeutically effective amount of a compound of Formula I, or pharmaceutically acceptable salt thereof.

The present compounds can be used to treat or reduce the risk of developing atherosclerosis in a patient in need of such treatment by administering to the patient a therapeutically effective amount of a compound of Formula I, or a pharmaceutically acceptable salt thereof.

The present compounds can be used to treat or reduce hyperglycemia in a diabetic patient in need of such treatment by administering to the patient a therapeutically effective amount of a compound of Formula I, or a pharmaceutically acceptable salt thereof.

The compounds may have utility in treating osteoporosis. The compounds of this invention may be used to treat osteoporosis or to reduce the risk of developing osteoporosis by slowing or stopping the loss of bone density in a patient who has osteoporosis or is at risk of developing osteoporosis. The compounds of this invention may also reverse the loss of bone mass in patients who have already begun to lose bone mass. In particular, the compounds can be used weekly, every other week, every third week, monthly or even less often, alone or in combination with other medications. Typical anti-osteoporosis medications that are useful herein with the compounds of formula I or a salt thereof, includes the bisphosphonates, such as alendroniate, risidronate, zoledrenic acid and the like; cathepsin K inhibitors, such as exenatide, liraglutide and the like; calcitonin and other medications.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (such as torcetrapib), niacin, niacin receptor agonists, bile acid sequestrants, microsomal triglyceride transport inhibitors, and bile acid reuptake inhibitors. These combination treatments may also be effective for the treatment or control of one or more related conditions selected from the group consisting of hypercholesterolemia, atherosclerosis, hyperlipidemia, hypertriglyceridemia, dyslipidemia, high LDL, and low HDL Another aspect of the invention that is of interest relates to a method of treating or controlling one or more of: mixed or diabetic dyslipidemia, hypercholesterolemia, atherosclerosis, low HDL levels, high LDL levels, hyperlipidemia, and/or hypertriglyceridemia, type 2 diabetes, hyperglycemia, insulin resistance and related conditions, which comprises administering to a patient in need of such treatment a therapeutically effective amount of a compound having formula I in combination with a compound selected from the group consisting of:

a DPP-4 antagonist; a glucagon receptor antagonist; a glucokinase activator; a GPR119 agonist; a GPR 40 modulator; a GPR 120 agonist; an insulin sensitizer; a sulfonylurea or other insulin secretagogue; a SPPARγM such as those disclosed in WO 2006/099077 A1; an α-glucosidase inhibitor; a GLP-1, GLP-1 analogue or mimetic or a GLP-1 receptor agonist; a GIP, GIP mimetic or GIP receptor agonist; a PACAP, a PACAP mimetic or PACAP receptor agonist; an HMG Co-A reductase inhibitor; a bile acid sequestrant; nicotinic acid or a nicotinyl alcohol; a PPAR α agonist; a PPARα/γ dual agonist; inhibitors of cholesterol absorption; acyl CoA: cholesterol acyltransferase inhibitors; antioxidants; PPARδ agonists; antiobesity agents such as NPY1 or NPY5 antagonists CB1 receptor inverse agonists, ileal bile acid transporter inhibitors; aspirin, NSAIDs, glucocorticoids, azulfidine, selective COX-2 inhibitors; antihypertensive agents such as ACE inhibitors, AII receptor blockers, beta blockers and calcium channel blocking drugs; inhibitors of 11β-HSD-1; inhibitors of CETP and inhibitors of fructose 1,6-bisphosphatase.

Another aspect of the invention provides a method of treating inflammatory conditions, including inflammatory bowel disease, Crohn's disease, and ulcerative colitis by administering an effective amount of a compound of this invention to a patient in need of treatment. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a weekly dosage of from about 0.05 milligrams to about 100 milligrams per kilogram of animal body weight, preferably given as a weekly dose, or in sustained release form. For most large mammals, including humans (e.g. a 70 kg adult), the total weekly dosage administered once weekly is from about 0.1 milligrams to about 1000 milligrams, is likely to be from about 0.5 milligrams to about 350 milligrams, and is often from about 1 milligram to about 50 milligrams. For a particularly potent compound, the dosage for an adult human may be as low as 0.1 mg. Examples of weekly dosages for a 70 kg adult human are 0.1 mg, 0.5 mg, 1 mg, 2 mg, 5 mg, 10 mg, 25 mg, 50 mg, 100 mg, 150 mg, 200 mg, 250 mg, 350 mg, and 500 mg per day. The dosage regimen may be adjusted within the above ranges or even outside of these ranges to provide the optimal therapeutic response.

Oral administration will usually be carried out using tablets. Examples of doses in tablets which may be administered once weekly include about 0.1 mg, 0.5 mg, 1 mg, 2 mg, 5 mg, 10 mg, 25 mg, 50 mg, 100 mg, 150 mg, 200 mg, 250 mg, 350 mg, and 500 mg. Other oral forms (e.g. capsules or suspensions) can also be administered in doses having similar sizes.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy. In general, compositions suitable for oral administration are preferred.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form, in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment or amelioration of one or more of the diseases or conditions for which compounds of Formula I are useful. Such other drugs may be administered, by a route and in an amount commonly used therefore, contemporaneously (such as via co-administration) or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other PPAR gamma agonists and partial agonists, such as the glitazones (e.g. troglitazone, pioglitazone, englitazone, MCC-555, rosiglitazone, balaglitazone, netoglitazone, and the like), and PPAR gamma agonists and partial agonists that do not have a glitazone structure (e.g. K-111, INT-131, MBX-102 [metaglidisen], MBX-2044, FK614 including SPPARγM GSK-376501 and the like);

(b) biguanides such as metformin and phenformin;

(c) protein tyrosine phosphatase-1B (PTP-1B) inhibitors, (d) dipeptidyl peptidase IV (DPP-4) inhibitors. including sitagliptin, vildagliptin, saxagliptin, as well as those disclosed in the following published patents and applications: U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-4 inhibitor compounds include isoleucine thiazolidide (P32/98); NVP-DPP-728; vildagliptin (LAF 237); P93/01; and saxagliptin (BMS 477118).

(e) insulin or insulin mimetics, including rapid acting insulin, regular insulin, long acting insulin, complexed forms of insulin and the like, administered by any conventional route, such as subcutaneous, intradermal or intramuscular injection, oral, transdermal, intranasal, intrapulmonary, and the like;

(f) insulin secretagogues, such as sulfonylureas (e.g. tolbutamide, glimepiride, and glipizide) and meglitinides (eg. repaglinide and nateglinide);

(g) α-glucosidase inhibitors (such as acarbose and miglitol);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) niacin receptor agonists, (v) PPARα agonists such as fenofibric acid derivatives (gemfibrozil, clofibrate, fenofibrate and bezafibrate), (vi) cholesterol absorption inhibitors, such as for example ezetimibe, (vii) acyl CoA:cholesterol acyltransferase (ACAT) inhibitors, such as avasimibe, (viii) CETP inhibitors, such as torcetrapib, JTT-705, and compounds disclosed in WO2005/100298, WO2006/014357, and WO2006/014413, and (ix) phenolic anti-oxidants, such as probucol;

(i) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and $β_3$ adrenergic receptor agonists;

(j) ileal bile acid transporter inhibitors;

(k) agents intended for use in inflammatory conditions such as aspirin, non-steroidal anti-inflammatory drugs, glucocorticoids, azulfidine, and cyclo-oxygenase 2 selective inhibitors;

(l) glucagon receptor antagonists;

(m) GLP-1;

(n) GIP-1; and (o) GLP-1 analogs, such as exendins, including exenatide;

(p) PPARδ agonists such as those disclosed in WO 97/28149; and (q) antihypertensives, such as diuretics, e.g., hydrochlorothiazide, furosemide and the like; beta adrenergic blocking drugs, such as propranolol, metaprolol and the like; ACE inhibitors, such as enalapril, lisinopril, ramipril, quinapril and the like, ARBs, such as losartan, valsartan, irbesartan, candesartan and the like, and calcium channel blocking drugs, such as amlodipine, diltiazem and verapamil.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DPP-4 inhibitors, and anti-obesity compounds.

Also claimed is the use of additional PPAR alpha, gamma or delta selective agonists, PPAR alpha/gamma, gamma/delta, alpha/delta dual agonists, or PPAR alpha/gamma/delta pan agonists on a once weekly basis. These agents are useful for the treatment of diabetes, dyslipidemia and weight loss. Examples of such agents include, but are not limited to the following: netoglitazone, pioglitazone, rosiglitazone, troglitazone, balaglitazone, CS204, AZD6610, ZYH1, GFT505, LY-465608, DRF-2519, DRF-11605, DRF-2725, GW-626019, GW-625019, CS038, ONO-5129, aleglitazar, muraglitazar, soldeglitazar, teseglitazar, naveglitazar, farglitazar, KRP-297, AVE0897, AVE 0847, LBM642, PPM263, PPM202, PPM201, PPM204, PLX-204, GW-677954, NN0606, AVE8134, NS-220, SAR 35034, KD3010, GW-501516, FK614, K-111, metaglidasen, MBX-2044, INT-131, KD3010, KR-62980, SVT002149, AVE8134, AVE5378, AVE0897, SAR35034, AVE5376, MBX2130, PAT-5A, GW-501516, GW-1262570, GW677954, GW590735, R-483, and BAY-54-9801.

Compounds of the present invention (i.e. compounds having Formula I) can be used to treat one or more diseases or conditions selected from hypercholesterolemia, atherosclerosis, low HDL levels, high LDL levels, hyperlipidemia, hypertriglyceridemia, and dyslipidemia by administering a therapeutically effective amount of a compound of claim 1 in combination with an HMG-CoA reductase inhibitor to a patient in need of such treatment. Statins are the preferred HMG-CoA reductase inhibitors for use in this combination therapy. Preferred statins include lovastatin, simvastatin, pravastatin, fluvastatin, atorvastatin, itavastatin, ZD-4522, rivastatin, and rosuvastatin. This combination treatment may be particularly desirable for treating or reducing the risk of developing atherosclerosis. Such a combination can optionally have a third pharmaceutically active ingredient, such as a CETP inhibitor (e.g. torcetrapib) or a cholesterol absorption inhibitor (e.g. ezetimibe).

The process for making the compounds used in the instant invention is generally described in WO2006/096564A1 published on Sep. 14, 2006.

Biological Assays

A) PPAR Binding Assays

For preparation of recombinant human PPARγ, PPARδ, and PPARα: Human PPARγ$_2$, human PPARγ and human PPARα were expressed as gst-fusion proteins in *E. coli*. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). *E. coli* containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C.

For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3H_2$] AD5075, (21 Ci/mmole), ±test compound as described in Berger et al (Novel peroxisome proliferator-activated receptor (PPARδ) and PPAR ligands produce distinct biological effects. J. Biol. Chem. (1999), 274: 6718-6725. Assays were incubated for ~16 hr at 4° C. in a final volume of 150 pt. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3H_2$]L-783483, (17 Ci/mmole), ±test compound as described in Berger et al (Novel peroxisome proliferator-activated receptory (PPARγ) and PPARδ ligands produce distinct biological effects. 1999 J Biol Chem 274: 6718-6725). (L-783483 is 3-chloro-4-(3-(7-propyl-3-trifluoromethyl-6-benz-[4,5]-isoxazoloxy)propylthio)phenylacetic acid, Ex. 20 in WO 97/28137). Assays were incubated for ~16 hr at 4° C. in a final volume of 150 μL. Unbound ligand was removed by incubation with 100 dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [$^3$H$_2$]L-797773, (34 Ci/mmole), ±test compound. (L-797733 is (3-(4-(3-phenyl-7-propyl-6-benz-[4,5]-isoxazoloxy)butyloxy))phenylacetic acid, Ex.62 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B) Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5×)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at 12×10$^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% CO$_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5×)-tk-luc reporter vector and 0.0002 μg of pCMV-lacZ as an internal control for transactivation efficiency. Cells were incubated in the transfection mixture for 5 h at 37° C. in an atmosphere of 10% CO$_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

Agonism is determined by comparison of maximal transactivation activity with a full PPAR agonist, such as rosiglitazone. Generally, if the maximal stimulation of transactivation is less than 50% of the effect observed with a full agonist, then the compound is designated as a partial agonist. If the maximal stimulation of transactivation is greater than 50% of the effect observed with a full agonist, then the compound is designated as a full agonist. The compounds of this invention generally have EC50 values in the range of 1 nM to 3000 nM.

C) In Vivo Studies

Male db/db mice (10-11 week old C57B1/KFJ, Jackson Labs, Bar Harbor, Me.) are housed 5/cage and allowed ad lib. access to ground Purina rodent chow and water. The animals, and their food, are weighed every 2 days and are dosed daily by gavage with vehicle (0.5% carboxymethylcellulose)±test compound at the indicated dose. Drug suspensions are prepared daily. Plasma glucose, and triglyceride concentrations are determined from blood obtained by tail bleeds at 3-5 day intervals during the study period. Glucose and triglyceride, determinations are performed on a Boehringer Mannheim Hitachi 911 automatic analyzer (Boehringer Mannheim, Indianapolis, Ind.) using heparinized plasma diluted 1:6 (v/v) with normal saline. Lean animals are age-matched heterozygous mice maintained in the same mariner.

Surprisingly when the compounds of formula I are administered to a patient on a once weekly basis, weight gain that is normally observed when these compounds are administered on a daily basis is not observed. This constitutes a surprising discovery that renders the weekly dosing regimen unexpectedly more useful than daily dosing.

What is claimed is:

1. A method of treating type 2 diabetes, comprising administering to a patient in need of such treatment, on a once weekly basis, a compound of formula I:

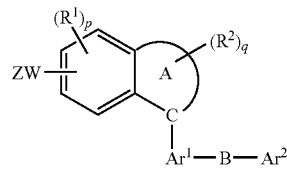

or a pharmaceutically acceptable salt thereof, wherein:

Ring A is a 5- or 6-membered aromatic or heteroaromatic ring having 1-2 heteroatoms independently selected from O, S, and N, wherein Ring A together with the phenyl ring to which ring A is fused forms a naphthalene or benzoheteroaromatic ring;

$A^1$ and $Ar^2$ are each carbocyclic or heterocyclic aromatic groups which are independently selected from the group consisting of phenyl, naphthyl, pyridinyl, pyrazinyl, and pyrimidinyl, said aromatic groups being optionally substituted with 1-4 substituent groups independently selected from halogen, —C$_1$-C$_6$ alkyl, —C$_2$-C$_6$ alkenyl, —C$_2$-C$_6$ alkynyl, —OC$_1$-C$_6$ alkyl, —OC$_2$-C$_6$ alkenyl, —C(=O)C$_1$-C$_6$ alkyl, —S(O)$_n$C$_1$-C$_6$ alkyl, C$_3$-C$_7$ cycloalkyl, —OC$_3$-C$_7$ cycloalkyl, —NO$_2$, and —CN, wherein —C$_1$-C$_6$ alkyl, —C$_2$-C$_6$ alkenyl, —C$_2$-C$_6$ alkynyl, —OC$_1$-C$_6$ alkyl, —OC$_2$-C$_6$ alkenyl, —C(=O)C$_1$-C$_6$ alkyl, —S(O)$_n$C$_1$-C$_6$ alkyl, C$_3$-C$_7$ cycloalkyl, and —OC$_3$-C$_7$ cycloalkyl are each optionally substituted with 1-5 halogens;

B is selected from the group consisting of —O—, —S(O)$_n$—, —N(R$^3$)—, —C(=O)—, —C(R$^4$)$_2$—, and —C$_{3-6}$ cycloalkylidene-;

—WZ is selected from the group consisting of —O—C(R$^5$)(R$^6$)—Z, —S(O)$_n$—C(R$^5$)(R$^6$)—Z, and —CH$_2$—C(R$^5$)(R6)—Z ;

Z is selected from the group consisting of —CO$_2$R$^7$ and tetrazole;

R$^1$ and R$^2$ are each independently selected from the group consisting of halogen, —CN, —NO$_2$, —OH, —C$_1$-C$_5$ alkyl, —OC$_1$-C$_5$ alkyl, —C(=O)C$_1$-C$_5$ alkyl, —S(O)$_n$C$_1$-C$_5$alkyl, and C$_{3-6}$ cycloalkyl, wherein C$_1$-C$_5$ alkyl, —OC$_1$-C$_5$ alkyl, —C(=O)C$_1$-C$_5$ alkyl, —S(O)$_n$C$_1$-C$_5$alkyl, and C$_{3-6}$ cycloalkyl are optionally substituted with 1-5 halogens;

R$^3$ is selected from the group consisting of H and C$_1$-C$_5$ alkyl;

each R$^4$ is independently selected from the group consisting of H, halogen, and —C$_1$-C$_5$ alkyl, wherein —C$_1$-C$_5$ alkyl is optionally substituted with 1-5 halogens;

R$^5$ and R6 are each independently selected from the group consisting of H, halogen, —C$_1$-C$_5$ alkyl, —OC$_1$-C$_5$ alkyl, —C$_2$-C$_5$ alkenyl, —OC$_2$-C$_5$ alkenyl, C$_{3-6}$ cycloalkyl, —(CH$_2$)$_m$phenyl, and —O(CH$_2$)$_m$phenyl, wherein —C$_1$-C$_5$ alkyl, —OC$_1$-C$_5$ alkyl, —C$_2$-C$_5$ alkenyl, and —OC$_2$-C$_5$ alkenyl are optionally substituted with 1-5 halogens, and wherein C$_{3-6}$ cycloalkyl and the phenyl of —(CH$_2$)$_m$phenyl and —O(CH$_2$)$_m$phenyl are optionally substituted with 1-5 groups independently selected from halogen, C$_1$-C$_3$ alkyl and —OC$_1$-C$_3$ alkyl, said C$_1$-C$_3$ alkyl and —OC$_1$-C$_3$ alkyl being optionally substituted with 1-3 halogens; or alternatively R$^5$ and R$^6$ may be joined to form a C$_3$-C$_6$ cycloalkyl group, said C$_3$-C$_6$ cycloalkyl group optionally being substituted with 1-3 halogens;

R$^7$ is selected from the group consisting of H and —C$_1$-C$_6$ alkyl, wherein C$_1$-C$_6$ alkyl is optionally substituted with 1-5 halogens;

m in each instance is an integer from 0-2;
n in each instance is an integer from 0-2;
p is an integer from 0 to 3; and
q is an integer from 0-3.

2. The method of claim 1, wherein Ring A together with the phenyl ring to which ring A is fused forms a naphthalene ring or a benzoheteroaromatic ring selected from the group consisting of quinolyl, isoquinolyl, benzisoxazolyl, indolyl, indazolyl, benzofuryl, and benzothienyl.

3. The method of claim 2 wherein:

Ring A together with the phenyl ring to which ring A is fused forms a naphthalene ring or a benzoheteroaromatic ring selected from the group consisting of quinolyl, benzisoxazolyl, indolyl, indazolyl, benzofuryl, and benzothienyl;

Ar$^1$ is selected from the group consisting of phenyl, pyrimidinyl, and pyridinyl, and Ar$^2$ is selected from the group consisting of phenyl and pyridinyl, wherein Ar$^1$ and Ar$^2$ are each optionally substituted with 1-4 substituent groups independently selected from halogen, —C$_1$-C$_4$ alkyl, —OC$_1$-C$_4$ alkyl, —S(O)$_n$C$_1$-C$_4$ alkyl, —NO$_2$, and —CN, wherein —C$_1$-C$_4$ alkyl, —OC$_1$-C$_4$ alkyl, and —S(O)$_n$C$_1$-C$_4$ alkyl are each optionally substituted with 1-3 halogens;

B is selected from —O— and —C(=O)—;

—WZ is —O—C(R$^5$)(R$^6$)—CO$_2$R$^7$;

R$^1$ and R$^2$ are each independently selected from the group consisting of halogen, —OH, —CN, —NO$_2$, —C$_1$-C$_3$ alkyl, —OC$_1$-C$_3$ alkyl, —S(O)$_2$CH$_3$, and —S(O)$_2$CF$_3$, wherein —C$_1$-C$_3$ alkyl and —OC$_1$-C$_3$ alkyl are optionally substituted with 1-3 halogens;

R$^5$ and R$^6$ are each independently selected from the group consisting of H, halogen, and —C$_1$-C$_4$ alkyl, wherein —C$_1$-C$_4$ alkyl is optionally substituted with 1-5 halogens;

R$^7$ is selected from the group consisting of H and C$_1$-C$_6$ alkyl, wherein C$_1$-C$_6$ alkyl is optionally substituted with 1-5 halogens;

n is an integer from 0-2;
p is an integer from 0 to 2; and
q is an integer from 0-2.

4. The method of claim 3 wherein:

Ring A together with the phenyl ring to which ring A is fused forms a naphthalene ring or a benzoheteroaromatic ring selected from the group consisting of benzisoxazolyl, indazolyl, and benzofuryl;

Aris selected from the group consisting of phenyl and pyridinyl, and is optionally substituted with 1-2 groups which are independently selected from C$_1$-C$_4$ alkyl, wherein C$_1$-C$_4$ alkyl is optionally substituted with 1-3 halogens;

Ar$_2$ is phenyl, which is optionally substituted with 1-2 substituent groups independently selected from halogen, —CN, —C$_1$-C$_3$ alkyl, and —OC$_1$-C$_3$ alkyl, wherein —C$_1$-C$_3$ alkyl and —OC$_1$-C$_3$ alkyl are optionally substituted with 1-3 halogens;

B is —O—;

—WZ is —O—C(R$^5$)(R$^6$)—CO$_2$H;

each R1 is independently selected from the group consisting of halogen, —C$_1$-C$_3$ alkyl, and —OH, wherein —C$_1$-C$_3$ alkyl is optionally substituted with 1-3 halogens;

Each R$^2$ is independently selected from the group consisting of —C$_1$-C$_3$ alkyl, —S(O)$_2$CH$_3$, and —S(O)$_2$CF$_3$, wherein —C$_1$-C$_3$ alkyl is optionally substituted with 1-3 halogens;

R$^5$ and R$^6$ are each independently H or —C$_1$-C$_3$ alkyl;
p is an integer from 0-2; and
q is an integer from 0-2.

5. The method of claim 1, wherein the compound is of Formula II:

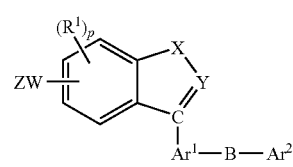

wherein:

X—Y is selected from the group consisting of —O—N=, —N(R$^2$)—N=, —O—C(R$^2$)=, —S—C(R2)=, and —N(R2)—(CR2)=.

6. The method of claim 5 wherein:

Ar$^1$ is selected from the group consisting of phenyl, pyrimidinyl, and pyridinyl, and is optionally substituted with 1-2 groups which are independently selected from C$_1$-C$_4$ alkyl, wherein C$_1$-C$_4$ alkyl is optionally substituted with 1-3 halogens;

Ar$^2$ is phenyl, which is optionally substituted with 1-2 substituent groups independently selected from halogen, —CN, —C$_1$-C$_3$ alkyl, and —OC$_1$-C$_3$ alkyl, wherein —C$_1$-C$_3$ alkyl and —OC$_1$-C$_3$ alkyl are optionally substituted with 1-3 halogens;

B is selected from —O— and —C(=O)—;

—WZ is —O—C(R$^5$)(R$^6$)—CO$_2$R$^7$;

each R$^1$ is independently selected from the group consisting of halogen, —C$_1$-C$_3$ alkyl, —OC$_1$-C$_3$ alkyl, and —OH, wherein —C$_1$-C$_3$ alkyl and —OC$_1$-C$_3$ alkyl are optionally substituted with 1-3 halogens;

each R2 is independently selected from the group consisting of H, —C$_1$-C$_3$ alkyl, —S(O)$_2$CH$_3$, and —S(O)$_2$CF$_3$, wherein —C$_1$-C3 alkyl is optionally substituted with 1-3 halogens;

R$^5$ and R$^6$ are each independently selected from the group consisting of H and C$_1$-C$_3$ alkyl, wherein —C$_1$-C$_3$ alkyl is optionally substituted with 1-5 halogens;

R$^7$ is H or —C$_1$-C$_5$ alkyl; and
p is an integer from 0-2.

7. The method of claim 1 wherein the compound is in accordance with formula III:

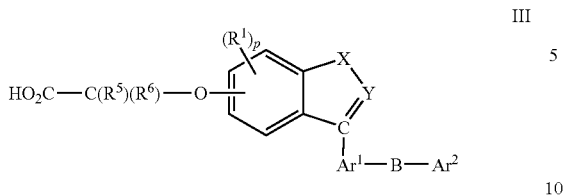

wherein:
- X—Y is selected from the group consisting of —O—N=, —N(R²)—N=, and —O—C(R²)=;
- Ar¹ is selected from the group consisting of phenyl, pyrimidinyl, and pyridinyl, wherein Ar¹ is optionally substituted with a —$C_2$-$C_4$ alkyl group, which is optionally substituted with 1-3 F;
- each R¹ is independently selected from the group consisting of halogen, $CH_3$, —$CF_3$, —OH, —$OCH_3$, and —$OCF_3$;
- R² is selected from the group consisting of H, —$C_1$-$C_3$ alkyl, —$CF_3$, —$S(O)_2CH_3$, and —$S(O)_2CF_3$;
- R⁵ is H or —$C_1$-$C_3$ alkyl; and
- R6 is —$C_1$-$C_3$ alkyl.

8. The method of claim 7 wherein:
- Ar¹ is selected from the group consisting of phenyl, pyrimidinyl, and pyridinyl, wherein pyridinyl is connected at the 3-position to the C-atom of the ring A to which Ar¹ is connected, pyrimidinyl is connected at the 5-position to the C-atom of the ring A to which Ar¹ is connected, and Ar¹ is substituted with one —C2-C4 alkyl substituent which is optionally substituted with 1-3 F;
- Ar² is phenyl, which is optionally substituted with 1-2 substituent groups independently selected from halogen, —CN, —$C_1$-$C_2$ alkyl, —$CF_3$, —$OCH_3$, and —OCF3;
- B is —O—;
- each R¹ is independently selected from the group consisting of halogen, —CH3, —$CF_3$, and —OH;
- R² is selected from the group consisting of H, —$CH_3$, —$CF_3$, —$S(O)_2CH_3$, and —$S(O)_2CF_3$;
- R⁵ is H or —$CH_3$; and
- R⁶ is —$C_1$-$C_3$ alkyl.

9. The method of claim 8 wherein the compound is in accordance with formula IV:

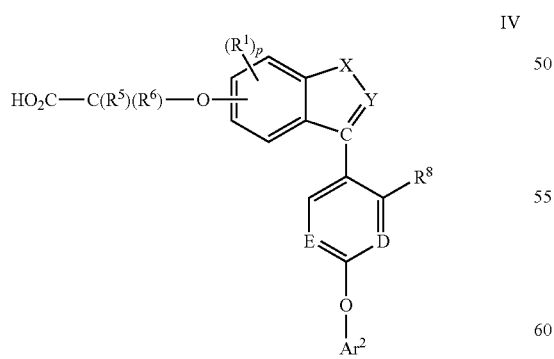

wherein:
- D and E are each independently selected from —CH= and —N=; and
- R⁸ is —$C_2$-$C_4$ alkyl, which is optionally substituted with 1-3 F.

10. The method of claim 9 wherein the compound is of Formula V:

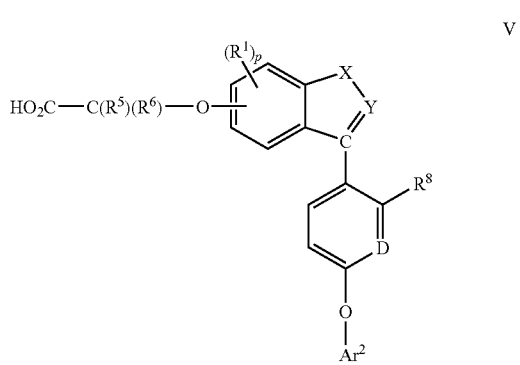

wherein:
- D is selected from —CH= and —N=; and
- R⁸ is —$C_2$-$C_4$ alkyl.

11. The method of claim 10 wherein:
- R⁸ is n-propyl;
- R² is H, —$CH_3$, or —$S(O)_2CH_3$; and
- R⁶ is $C_1$-$C_2$ alkyl.

12. The method of claim 11, wherein: X—Y represents —O—N=; and D represents —N=.

13. The method of claim 1 wherein the compound administered on a weekly basis is selected from the group consisting of:

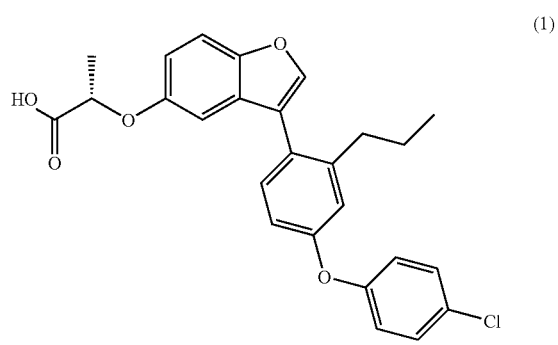

(1)

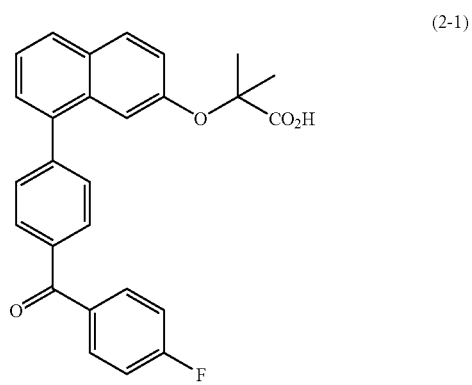

(2-1)

(2)
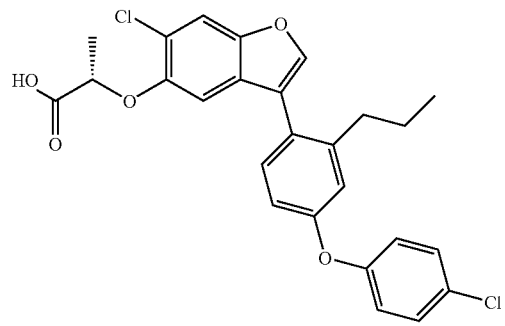
(2-2)
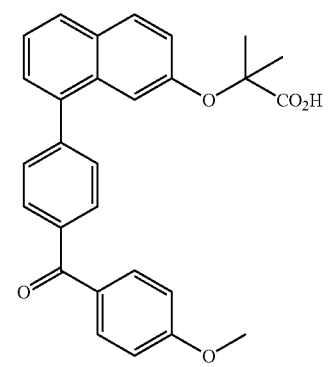
(3)
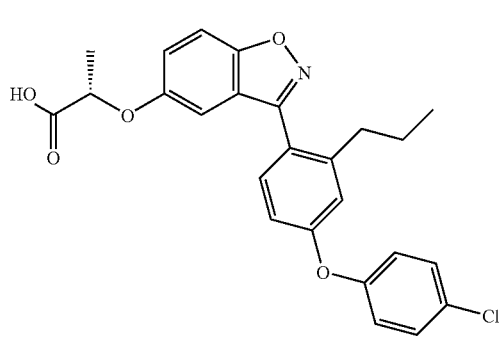
(2-3)
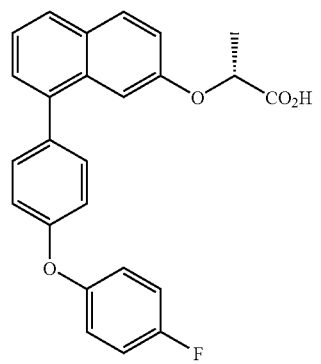
(4)
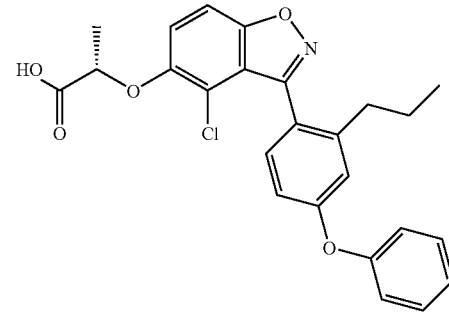
(2-4)
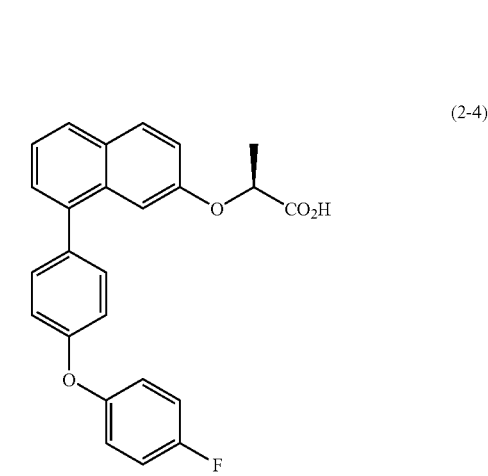
(5)
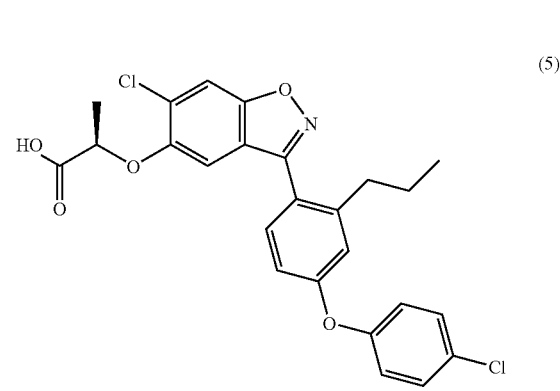
(2-5)
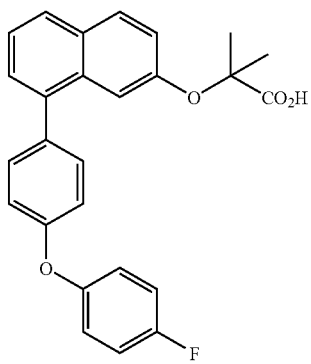

-continued
(6)
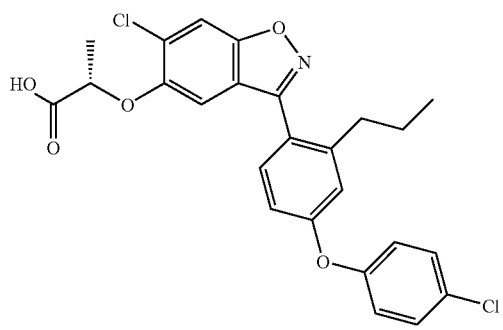
(2-6)
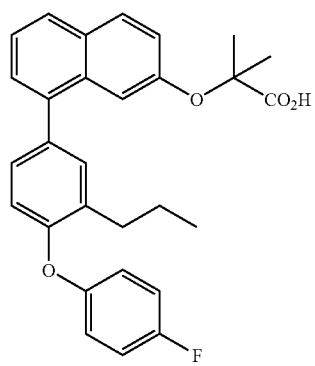
(7)
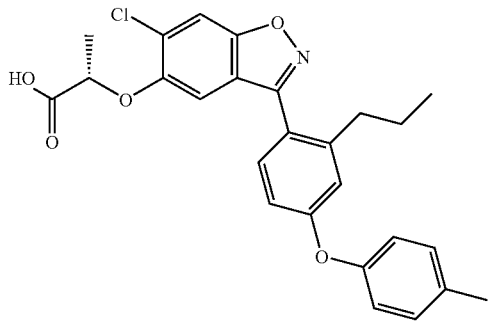
(2-7)
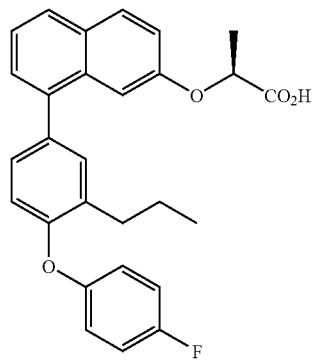
-continued
(8)
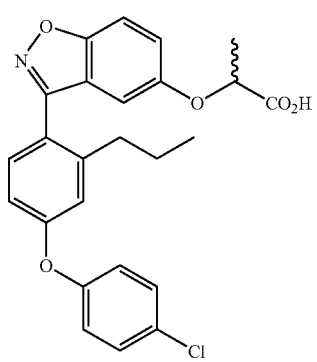
(2-8)
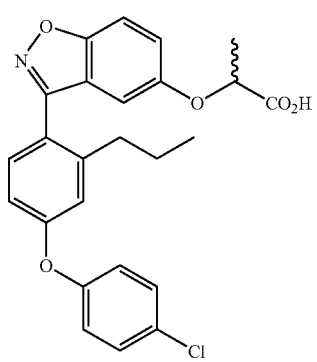
(9)
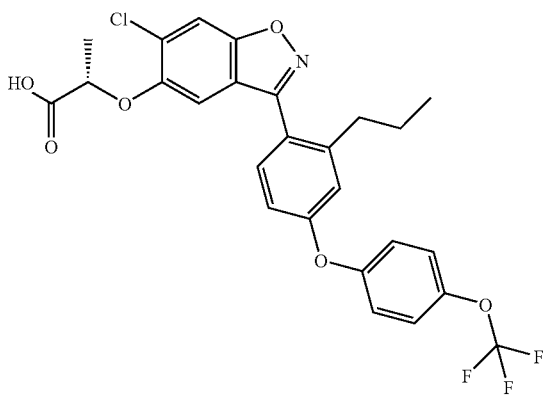
(2-9)
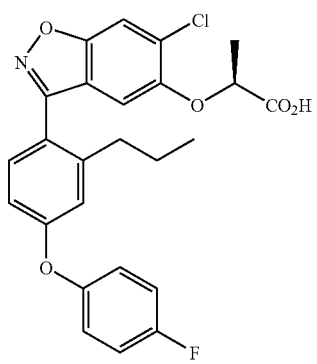

(10)
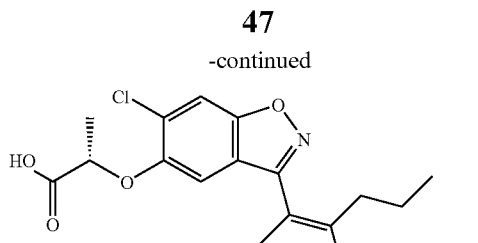
(2-10)
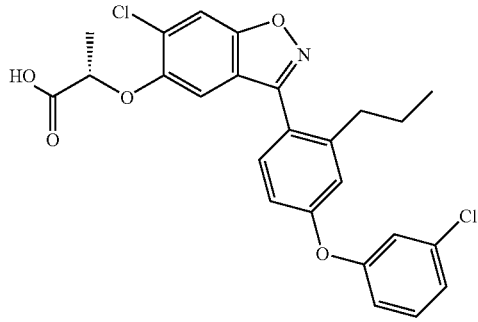
(11)
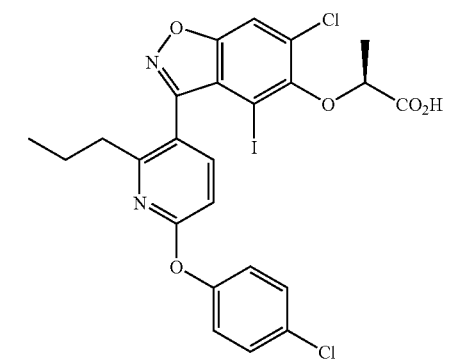
(12)
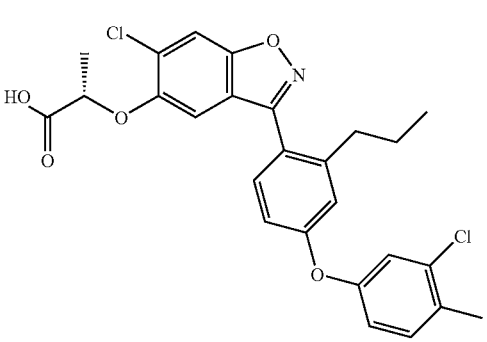
(13)
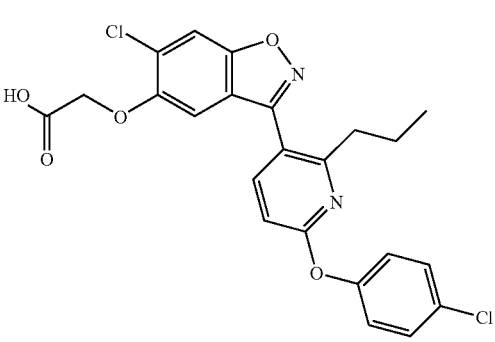
(14)
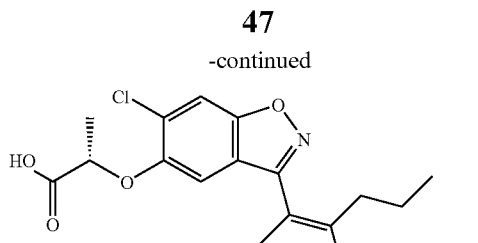
(15)
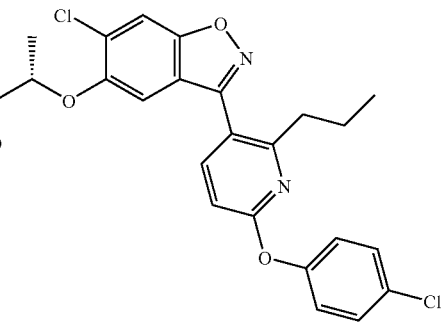
(16)
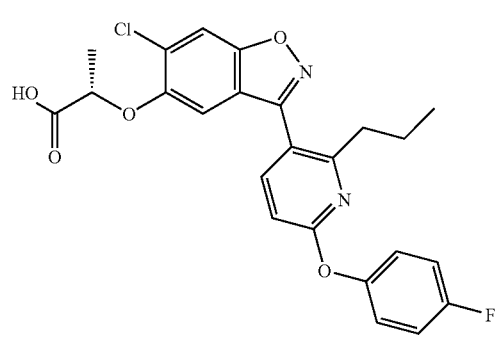
(17)
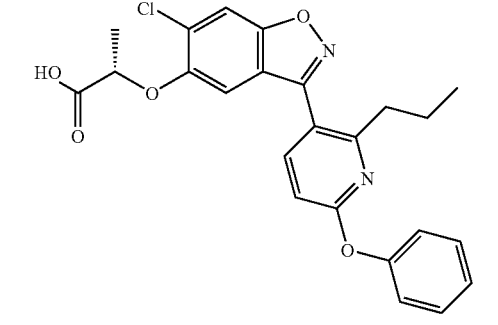
(18)
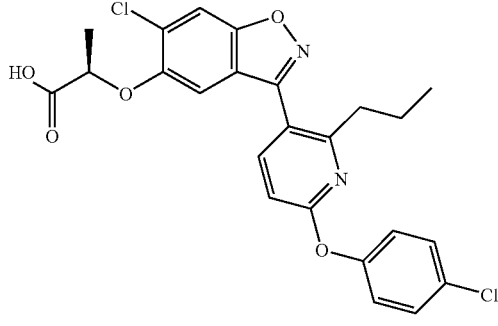

-continued
(19) 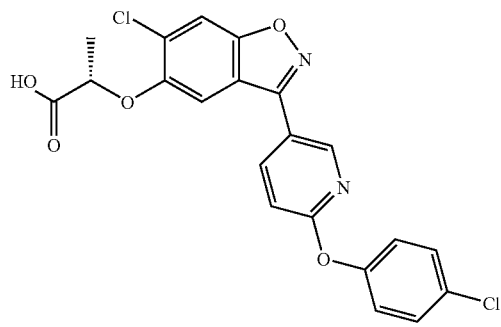
(20) 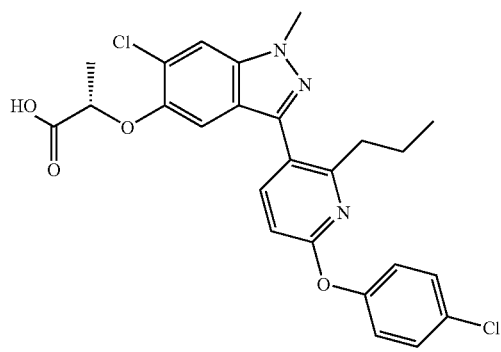
(21) 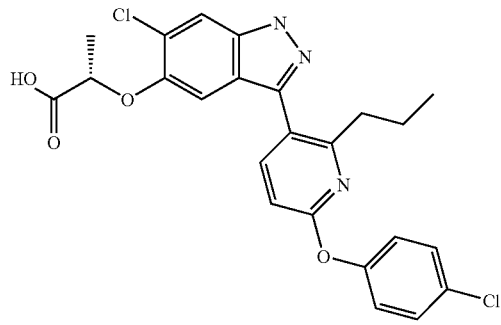
(22) 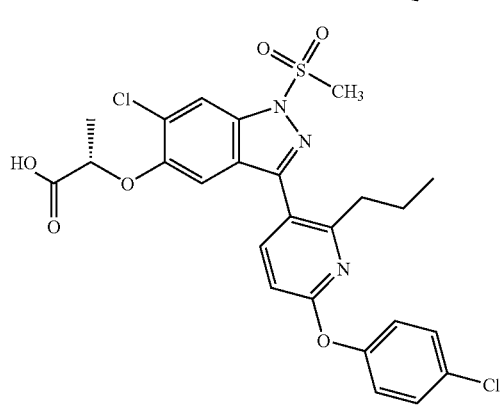
-continued
(23) 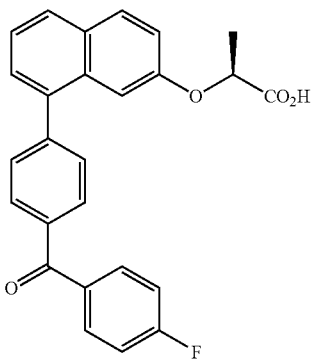
(24) 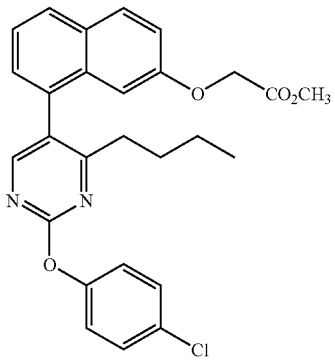
or a pharmaceutically acceptable salt thereof.
14. A method of treating type 2 diabetes, comprising administering to a patient in need of such treatment, on a once weekly basis, a compound which is:
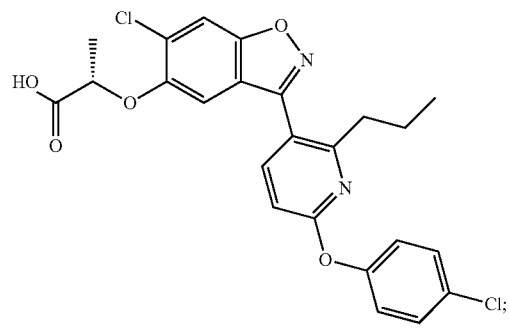
or a pharmaceutically acceptable salt thereof.
* * * * *